United States Patent
Black et al.

(10) Patent No.: US 9,788,790 B2
(45) Date of Patent: Oct. 17, 2017

(54) OPTICAL COHERENCE TOMOGRAPHY FOR BIOLOGICAL IMAGING

(75) Inventors: John F. Black, San Mateo, CA (US); Maegan K. Spencer, Mountain View, CA (US); Michael Zung, San Carlos, CA (US); Charles W. McNall, Belmont, CA (US); Evangeline Lumabas, San Jose, CA (US); Michael H. Rosenthal, San Carlos, CA (US); John B. Simpson, Woodside, CA (US)

(73) Assignee: AVINGER, INC., Redwood City, CA (US)

( * ) Notice: Subject to any disclaimer, the term of this patent is extended or adjusted under 35 U.S.C. 154(b) by 1311 days.

(21) Appl. No.: 12/790,703

(22) Filed: May 28, 2010

(65) Prior Publication Data

US 2010/0305452 A1 Dec. 2, 2010

Related U.S. Application Data

(60) Provisional application No. 61/182,061, filed on May 28, 2009, provisional application No. 61/258,064, (Continued)

(51) Int. Cl.
*A61B 8/00* (2006.01)
*A61B 5/00* (2006.01)

(52) U.S. Cl.
CPC .......... *A61B 5/6852* (2013.01); *A61B 5/0066* (2013.01)

(58) Field of Classification Search
CPC ........ A61B 8/00; A61B 5/0066; G02B 21/18; G01N 21/17
(Continued)

(56) References Cited

U.S. PATENT DOCUMENTS 4,178,935 A 12/1979 Gekhaman et al.
4,527,553 A 7/1985 Upsher
(Continued)

FOREIGN PATENT DOCUMENTS

CN 1875242 A 12/2006
CN 1947652 A 4/2007
(Continued)

OTHER PUBLICATIONS

Sharma et al.; Optical coherence tomography based on an all-fiber autocorrelator using probe-end reflection as reference; CWJ13; San Francisco, California, CLEO 2004.
(Continued)

*Primary Examiner* — Joseph M Santos Rodriguez
(74) *Attorney, Agent, or Firm* — Shay Glenn LLP

(57) ABSTRACT

Described herein are catheters for use with Optical Coherence Tomography (OCT) that include an optical fiber core having a first refractive index and an interface medium having a second refractive index, where the first and second refractive indexes are mismatched such that receiving electronics configured to receive optical radiation reflected from the reference interface and the target operate in a total noise range that is within 5dB of the shot noise limit. These OCT catheters may include a silicon die mirror having a reflective coating that is embedded in the interface medium. The optical fiber can be fixed at just the distal end of the catheter, and may be managed within a handle that is attached to the proximal end of the catheter body, and is configured to allow rotation of both the catheter body and the optical fiber relative to the handle.

25 Claims, 17 Drawing Sheets

Related U.S. Application Data filed on Nov. 4, 2009, provisional application No. 61/222,238, filed on Jul. 1, 2009.

(58) Field of Classification Search
USPC ....... 600/160, 459, 466, 476, 478; 356/3.02, 356/3.06, 3.08, 4.01, 450, 458; 359/212.01, 212.02, 214.1, 224.1, 224.2
See application file for complete search history.

(56) References Cited

U.S. PATENT DOCUMENTS

| | | |
|---|---|---|
| 4,552,554 A | 11/1985 | Gould et al. |
| 4,621,353 A * | 11/1986 | Hazel et al. ............... 369/44.23 |
| 4,639,091 A * | 1/1987 | Huignard et al. ............ 349/202 |
| 4,654,024 A | 3/1987 | Crittenden et al. |
| 4,686,982 A | 8/1987 | Nash |
| 4,771,774 A | 9/1988 | Simpson et al. |
| 4,841,977 A | 6/1989 | Griffith et al. |
| 4,926,858 A | 5/1990 | Gifford, III et al. |
| 5,000,185 A | 3/1991 | Yock |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A * | 7/1994 | Scheps ............................ 372/22 |
| 5,358,472 A | 10/1994 | Vance et al. |
| 5,383,460 A | 1/1995 | Jang et al. |
| 5,383,467 A | 1/1995 | Auer et al. |
| 5,429,136 A | 7/1995 | Milo et al. |
| 5,431,673 A | 7/1995 | Summers et al. |
| 5,459,570 A | 10/1995 | Swanson et al. |
| 5,465,147 A | 11/1995 | Swanson |
| 5,507,795 A | 4/1996 | Chiang et al. |
| 5,556,405 A | 9/1996 | Lary |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,868,778 A | 2/1999 | Gershony et al. |
| 5,872,879 A | 2/1999 | Hamm |
| 5,904,651 A | 5/1999 | Swanson et al. |
| 5,907,425 A * | 5/1999 | Dickensheets et al. ... 359/224.1 |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Patages et al. |
| 6,542,665 B2 | 4/2003 | Reed et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,623,496 B2 | 9/2003 | Snow et al. |
| 6,638,233 B2 | 10/2003 | Corvi et al. |
| 6,645,217 B1 | 11/2003 | MacKinnon et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |

(56) References Cited

U.S. PATENT DOCUMENTS

| | | |
|---|---|---|
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,313,493 B2 | 11/2012 | Fisher |
| 8,548,603 B2 | 10/2013 | Swoyer et al. |
| 2001/0020126 A1 | 9/2001 | Swanson et al. |
| 2002/0019644 A1 | 2/2002 | Hastings et al. |
| 2002/0077642 A1 | 6/2002 | Patel et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1* | 10/2002 | Wood ................ 310/307 |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1* | 5/2003 | Frot ................ 356/128 |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1* | 3/2004 | Yamada ........ G02B 6/1228 385/43 |
| 2004/0082850 A1 | 4/2004 | Bonner et al. |
| 2004/0092915 A1 | 5/2004 | Levatter |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1* | 10/2004 | Ghiron et al. .......... 385/36 |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1* | 6/2005 | Warden et al. ............. 385/141 |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1* | 10/2006 | Schmitt et al. ............. 600/478 |
| 2006/0244973 A1* | 11/2006 | Yun et al. ............. 356/511 |
| 2006/0252993 A1 | 11/2006 | Freed et al. |
| 2006/0264741 A1 | 11/2006 | Prince |
| 2006/0264743 A1 | 11/2006 | Kleen et al. |
| 2007/0010840 A1 | 1/2007 | Rosenthal et al. |
| 2007/0015969 A1* | 1/2007 | Feldman et al. ............. 600/160 |
| 2007/0015979 A1 | 1/2007 | Redel |
| 2007/0035855 A1* | 2/2007 | Dickensheets ............. 359/819 |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1* | 4/2007 | Brown et al. ............. 356/479 |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1* | 2/2008 | Seitz ............. 356/521 |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1* | 8/2008 | Xie ............. 356/450 |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |

(56) References Cited

U.S. PATENT DOCUMENTS

| | | |
|---|---|---|
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1* | 3/2009 | Wang ............ 356/369 |
| 2009/0093764 A1 | 4/2009 | Pfeffer et al. |
| 2009/0099641 A1 | 4/2009 | Wu et al. |
| 2009/0135280 A1 | 5/2009 | Johnston et al. |
| 2009/0137893 A1 | 5/2009 | Seibel et al. |
| 2009/0152664 A1* | 6/2009 | Klem et al. ............ 257/440 |
| 2009/0185135 A1* | 7/2009 | Volk ............ 351/219 |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0264826 A1 | 10/2009 | Thompson |
| 2009/0270888 A1 | 10/2009 | Patel et al. |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Miao et al. |
| 2011/0040238 A1 | 2/2011 | Wulfman et al. |
| 2011/0058250 A1 | 3/2011 | Liu et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2012/0041307 A1 | 2/2012 | Patel et al. |
| 2012/0046679 A1 | 2/2012 | Patel et al. |
| 2012/0238869 A1 | 9/2012 | Schmitt et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0289392 A1 | 10/2013 | Patel et al. |
| 2013/0296695 A1 | 11/2013 | Spencer et al. |
| 2014/0005534 A1 | 1/2014 | He et al. |
| 2014/0213893 A1 | 7/2014 | Simpson et al. |
| 2015/0099984 A1 | 4/2015 | Kankaria |
| 2015/0126856 A1 | 5/2015 | Tachibana et al. |
| 2015/0141816 A1 | 5/2015 | Gupta et al. |
| 2015/0208922 A1 | 7/2015 | Newhauser et al. |
| 2016/0008025 A1 | 1/2016 | Gupta et al. |
| 2016/0029902 A1 | 2/2016 | Smith et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010518900 A | 6/2010 |
| JP | 2012533353 A | 12/2012 |
| KR | 2007/0047221 | 5/2007 |
| RU | 2185859 C2 | 7/2002 |
| RU | 2218191 C2 | 12/2003 |
| WO | WO 91/017698 A1 | 11/1991 |
| WO | WO 99/23958 A1 | 5/1999 |
| WO | WO 00/54659 A1 | 9/2000 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO 2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO 2009/005779 A1 | 1/2009 |
| WO | WO 2009/006335 A1 | 1/2009 |
| WO | WO 2009/009799 A1 | 1/2009 |
| WO | WO 2009/009802 A1 | 1/2009 |
| WO | WO 2009/023635 A | 2/2009 |
| WO | WO 2009/024344 A1 | 2/2009 |
| WO | WO 2009/094341 A2 | 7/2009 |
| WO | WO 2009/140617 A2 | 11/2009 |
| WO | WO 2010/039464 A1 | 4/2010 |
| WO | WO 2010/056771 A1 | 5/2010 |

OTHER PUBLICATIONS

Simpson et. al; U.S. Appl. No. 13/433,049 entitled "Occlusion-Crossing Devices, Imaging, and Atherectomy Devices," filed Mar. 28, 2012.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

(56) References Cited

OTHER PUBLICATIONS

Wang et al.; Common-path endoscopic Fourier domain OCT with a reference Michelson interferometer; Proceedings of the SPIE; vol. 7566; pp. 75660L-75660L-7; Jan. 2010.
Patel et al.; U.S. Appl. No. 12/689,748 entitled "Guidewire support catheter," filed Jan. 19, 2010.
Rosenthal et al.; U.S. Appl. No. 12/829,277 entitled "Atherectomy catheter with laterally-displaceable tip," filed Jul. 1, 2010.
Spencer et al.; U.S. Appl. No. 12/829,267 entitled "Catheter-based off-axis optical coherence tomography imaging system," filed Jul. 1, 2010.
Aziz et al.; Chronic total occlusions—a stiff challege requiring a major breakthrough: is there light at the end of the tunnel?; Heart; vol. 91; suppl. III; pp. 42-48; 2005.
He et al.; U.S. Appl. No. 12/963,536 entitled "Devices and methods for predicting and preventing restenosis," filed Dec. 8, 2010.
Emkey et al.; Analysis and evaluation of graded-index fiber-lenses; Journal of Lightwave Technology; vol. LT-5; No. 9; pp. 1156-1164; Sep. 1987.
Linares et al.; Arbitrary single-mode coupling by tapered and nontapered grin fiber lenses; Applied Optics; vol. 29; No. 28; pp. 4003-4007; Oct. 1, 1990.
Suparno et al.; Light scattering with single-mode fiber collimators; Applied Optics; vol. 33; No. 30; pp. 7200-7205; Oct. 20, 1994.
Gonzalo et al.; Optical coherence tomography patterns of stent restenosis; Am. Heart J.; 158(2); pp. 284-293; Aug. 2009.
Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.
Simpson et al.; U.S. Appl. No. 14/424,266 entitled "Re-entry stylet for catheter," filed Feb. 26, 2015.
Simpson et al.; U.S. Appl. No. 14/424,277 entitled "Balloon atherectomy catheters with imaging," filed Feb. 26, 2015.
Simpson et al.; U.S. Appl. No. 15/072,272 entitled "Atherectomy catheters devices having multi-channel bushings," filed Mar. 16, 2016.
Patel et al.; U.S. Appl. No. 15/076,568 entitled "Atherectomy catheters and occlusion crossing devices," filed Mar. 21, 2016.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.

\* cited by examiner

| Low Ref Power | Ref Power | Sample Power | Shot Noise | Thermal Noise | Excess Noise | Total Noise | SNR | SNR (dB) | SNL-SNR | (dB) | SNR Degradation |
|---|---|---|---|---|---|---|---|---|---|---|---|
| -7.60 | 2.51E-08 | 2.5E-09 | 1.61E-22 | 3.31E-22 | 1.01E-23 | 5.02E-22 | 2.50E+05 | 5.40E+01 | 7.80E+05 | 5.89E+01 | 4.94E+00 |
| -7.40 | 3.98E-08 | 2.5E-09 | 2.55E-22 | 3.31E-22 | 2.54E-23 | 6.12E-22 | 3.25E+05 | 5.51E+01 | 7.80E+05 | 5.89E+01 | 3.80E+00 |
| -7.20 | 6.31E-08 | 2.5E-09 | 4.04E-22 | 3.31E-22 | 6.38E-23 | 7.99E-22 | 3.95E+05 | 5.60E+01 | 7.80E+05 | 5.89E+01 | 2.96E+00 |
| -7.00 | 1.00E-07 | 2.5E-09 | 6.41E-22 | 3.31E-22 | 1.60E-22 | 1.13E-21 | 4.42E+06 | 5.64E+01 | 7.80E+05 | 5.89E+01 | 2.47E+00 |
| -6.80 | 1.58E-07 | 2.5E-09 | 1.02E-21 | 3.31E-22 | 4.03E-22 | 1.75E-21 | 4.53E+05 | 5.66E+01 | 7.80E+05 | 5.89E+01 | 2.36E+00 |
| -6.60 | 2.51E-07 | 2.5E-09 | 1.61E-21 | 3.31E-22 | 1.01E-21 | 2.95E-21 | 4.25E+05 | 5.63E+01 | 7.80E+05 | 5.89E+01 | 2.63E+00 |
| -6.40 | 3.98E-07 | 2.5E-09 | 2.55E-21 | 3.31E-22 | 2.54E-21 | 5.42E-21 | 3.67E+05 | 5.56E+01 | 7.80E+05 | 5.89E+01 | 3.27E+00 |
| -6.20 | 6.31E-07 | 2.5E-09 | 4.04E-21 | 3.31E-22 | 6.38E-21 | 1.08E-20 | 2.93E+05 | 5.47E+01 | 7.80E+05 | 5.89E+01 | 4.25E+00 |

FIG. 3C

OPTICAL COHERENCE TOMOGRAPHY FOR BIOLOGICAL IMAGING

CROSS REFERENCE TO RELATED APPLICATIONS

This application claims the benefit of U.S. Provisional Application No. 61/182,061, filed May 28, 2009, U.S. Provisional Application No. 61/258,064, filed Nov. 4, 2009, and U.S. Provisional Application No. 61/222,238, filed Jul. 1, 2009. The disclosures of these applications are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are imaging devices and systems for use in biological probes. In particular, described herein are catheter-based imaging systems using Optical Coherence Tomography (OCT).

BACKGROUND OF THE INVENTION

In cardiovascular surgery, as well as other medical applications, there is frequently a need to extend very thin (few millimeter diameter), long (30-150+ cm) and sterile catheters into thin-walled (e.g., 1-1.5 millimeter wall thickness) biological lumens, including blood vessels such as arteries and veins.

A number of vascular diseases, such as coronary artery disease and peripheral vascular disease, are caused by the build-up of atherosclerotic deposits (plaque) in the arteries, which limit blood flow to the tissues that are supplied by that particular artery. Disorders caused by occluded body vessels, including coronary artery disease (CAD) and peripheral artery disease (PAD) may be debilitating and life-threatening. Chronic Total Occlusion (CTO) can result in limb gangrene, requiring amputation, and may lead to other complications and eventually death. Increasingly, treatment of such blockages may include interventional procedures in which a guidewire is inserted into the diseased artery and threaded to the blocked region. There the blockage may be either expanded into a more open position, for example, by pressure from an inflated catheter balloon (e.g., balloon angioplasty), and/or the blocked region may be held open by a stent. Treatment of such blockages can also include using a catheter to surgically remove the plaque from the inside of the artery (e.g., an atherectomy).

When the artery is totally blocked by plaque, it is extremely difficult, and potentially dangerous to force the guidewire through the occlusion. An obstruction or plaque may be composed of relatively tough fibrous material, often including hard calcium deposits. Forcing a guidewire or catheter past such obstructions may cause the guidewire to puncture the walls of the vessel (e.g., artery) or cause it to enter the layers forming the artery, further damaging the tissue. Thus, there remains a need for guidewire positioning devices that can effectively traverse occluded vessels, and particularly chronically occluded vessels. Such devices would enable positioning of a guidewire and therefore enable positioning of stents and other devices, leading to improved patient outcomes and a reduction in patient morbidity and mortality.

Moreover, there is medical interest in equipping catheter-based cardiovascular catheters with sensors that can help direct atherectomy and other surgical procedures. For example, it would be useful to have sensors that can give the surgeon immediate visual feedback as to whether a particular tissue is diseased and/or how far away the cutting portion of a catheter is from the boundary of a particular blood vessel layer to minimize the risk of accidental damage. Conventional radiological imaging methods and ultrasound imaging systems have been attempted for such surgical procedures. However, neither ultrasound nor radiological imaging methods have enough resolution to help guide the operation of the catheter over the critical last fraction of a millimeter between the interior of a blood vessel and the exterior of the blood vessel. Moreover, standard radiological techniques cannot easily discriminate between healthy tissue and diseased tissue unless the tissue has become heavily calcified. Further, the components of an ultrasound system are generally too large to implement in small dimensions.

Optical Coherence Tomography (OCT) has been proposed as one technique that may be particularly helpful for imaging regions of tissue, including within a body lumen such as a blood vessel. At a basic level, OCT relies on the fact that light traveling from a source and scattering from more distant objects takes longer to travel back than light scattering from nearby objects. Due to the wave nature of light, very small timing differences caused by light signals traveling different distances on the micron scale can cause constructive or destructive interference with reference light signals. OCT systems measure the resulting interference to obtain an image of the target. Unfortunately, however it has thus far proven difficult to provide stable and reliable OCT systems for use in a catheter. A typical OCT system requires one or more interferometers to distinguish the signal from the applied light. In addition, most known OCT systems, when applied to catheters, include a fiber that is rotated (often at high rates) within the catheter in order to scan around a lumen. These systems typically require relatively high power operation, since the many components necessary for rotating and managing the OCT pathway (e.g., fiber) result in optical losses.

Thus, there is a need for efficient and robust OCT systems that are compatible with catheter applications and uses. Described herein are enhanced Optical Coherence Tomography (OCT) systems that that overcome many of the problems described above.

Referring to FIG. 1, a typical OCT device includes a target arm and a reference arm to generate a reference signal. In order to provide the interference reference signal, the OCT device will split an illuminating light signal from the source in two equal or unequal parts, send part of the illuminating light to the target of interest through one target optical "target arm" and send the other part of the illuminating light down a separate reference arm. Light from the separate reference arm reflects off of a mirror, and then returns and interferes with the scattered light that is returning from the target optical arm after bouncing off of the target. In a traditional OCT device, the reference arm length is engineered to be exactly the same length as the target arm so that the interference effect is maximized. The resulting interference between the two beams creates interference effects known as fringes that can be used to measure the relative reflectivity of various layers of the target. Using this information, an image of the object can be generated.

By contrast to the more established applications for OCT, cardiovascular catheters, which are intended for one-time use in blood vessel environments, must be of the highest level of sterility. To obtain such sterility, cardiovascular catheters are typically produced as low-cost disposable items that can be factory sterilized. During a medical procedure, such a catheter is typically removed from the factory sterile container. The proximal end of the catheter is connected to equipment needed to control the catheter (which in this case would also include the link to the OCT engine used to drive any OCT optical fiber in the catheter), and the distal tip is immediately inserted into the patient's body. The catheter is then discarded once the procedure is complete.

Producing low-cost disposable catheters can be difficult as a result of the need for precise reference arm matching and expensive optics. Thus, there is also a need for a low-cost OCT catheter.

SUMMARY OF THE INVENTION

Described herein are OCT catheter, catheter systems, and methods of using and manufacturing them. In general, the OCT catheters and systems described herein are appropriate for use in a patient in order to visualize the internal structures within a lumen of the body in real time. These systems may allow control and navigation of the catheter, including navigation around and through complex anatomy such as bifurcations, ostials, regions of tortuosity, and the like. Further, the real-time and efficient imaging, as well as the control of the imaging system may allow a reduction in procedure time and improvements for long- and short-term outcomes.

In general, a system for optical coherence tomography may include a source of optical radiation, an optical fiber, receiving electronics, an interface medium, and a processor. Typically, the optical fiber has a core providing a common path for optical radiation reflected from a reference interface and a target. The core has a first refractive index. As described herein, the receiving electronics are configured to receive the optical radiation reflected from the reference interface and the target. The interface medium is at the reference interface and in optical contact with the optical fiber. The interface medium has a second refractive index. The first refractive index and the second refractive index are mismatched such that the receiving electronics operate in a total noise range that is within 5 dB of the shot noise limit. The processor generates an image of the target based upon the optical radiation received by the receiving electronics.

This and other embodiments may include one or more of the following features. The first refractive index and the second refractive index can be mismatched such that the receiving electronics operate in a total noise range that is within 3 dB of the shot noise limit. The first refractive index and the second refractive index can be mismatched such that the receiving electronics operate in a total noise range that is within 2 dB of the shot noise limit. The source of optical radiation can be a swept-frequency source.

The system can further include a mirror in the interface medium, and the mirror can be configured to reflect the optical radiation from the optical fiber to the target. The mirror can include a gold-coated silicon die. The interface medium can be a solid transparent medium. The interface medium can be in optical contact with a distal end of the core.

The system can further include a directional element configured to relay the optical radiation from the source to a distal end of the core.

The first refractive index $n_1$ and the second refractive index $n_2$ can be mismatched such that:

$$\frac{P_{out}}{P_{in}} = \left(\frac{n_1 - n_2}{n_1 + n_2}\right)$$

wherein $P_{in}$ is the power of the optical radiation at the distal end of the optical fiber prior to entering the interface medium, and wherein $P_{out}$ is the power of the optical radiation reflected from the reference interface such that the receiving electronics operate in a total noise range that is within 5 dB of the shot noise limit. In general, a catheter for use with optical coherence tomography includes an elongate catheter body, an optical fiber in the elongate catheter body, and an interface medium. The optical fiber has a core providing a common path for optical radiation reflected from a reference interface and a target. The core has a first refractive index. The interface medium is in optical contact with the optical fiber. The interface medium has a second refractive index. The first refractive index and the second refractive index are mismatched such that receiving electronics configured to receive optical radiation reflected from the reference interface and the target operate in a total noise range that is within 5 dB of the shot noise limit.

This and other embodiments may include one or more of the following features. The first refractive index and the second refractive index can be mismatched such that the receiving electronics operate in a total noise range that is within 3 dB of the shot noise limit. The first refractive index and the second refractive index can be mismatched such that the receiving electronics operate in a total noise range that is within 2 dB of the shot noise limit.

The system can further include a mirror in the interface medium. The mirror can be configured to reflect the optical radiation from the optical fiber to the target. The mirror can include a gold-coated silicon die. The interface medium can be a solid transparent medium. The interface medium can be in optical contact with a distal end of the core.

The first refractive index $n_1$ and the second refractive index $n_2$ can be mismatched such that:

$$\frac{P_{out}}{P_{in}} = \left(\frac{n_1 - n_2}{n_1 + n_2}\right)$$

wherein $P_{in}$ is the power of the optical radiation at the distal end of the optical fiber prior to entering the interface medium, and wherein $P_{out}$ is the power of the optical radiation reflected from the reference interface such that the receiving electronics operate in a total noise range that is within 5 dB of the shot noise limit.

In general, a method of performing optical coherence tomography includes: transmitting optical radiation from a source through an optical fiber having a core, the core having a first refractive index; transmitting the optical radiation from the optical fiber through an interface medium, wherein the interface medium is in optical contact with the optical fiber, the interface medium having a second refractive index; transmitting optical radiation reflected from the target and reflected from a reference interface along a common path in the optical fiber to a detector; receiving the reflected optical radiation at receiving electronics, wherein the first refractive index and the second refractive index are mismatched such that the receiving electronics operate in a total noise range that is within 5 dB of the shot noise limit;

and generating an image of the target based upon the reflected optical radiation received by the receiving electronics.

This and other embodiments may include one or more of the following features. The first refractive index and the second refractive index can be mismatched such that the receiving electronics operate in a total noise range that is within 3 dB of the shot noise limit. The first refractive index and the second refractive index can be mismatched such that the receiving electronics operate in a total noise range that is within 2 dB of the shot noise limit.

Transmitting, optical radiation can include transmitting optical radiation comprises transmitting swept-source radiation. Transmitting optical radiation from the optical fiber through the interface medium further can include transmitting the optical radiation from the optical fiber to a mirror in the interface medium.

In general, a system for optical coherence tomography includes a source of optical radiation, an optical fiber providing a common path for optical radiation reflected from a reference and a target, a detector to receive the optical radiation reflected from the reference and the target, an interface medium at the reference interface and in optical contact with the distal end of the optical fiber, a mirror in the embedding medium, and a processor to generate an image of the target based upon the optical radiation received by the detector. The mirror includes a silicon die having a reflective coating.

This and other embodiments may include one or more of the following features. The reflective coating can be metallic. The metallic coating can be gold. The reflective coating may be at least $$\frac{\lambda_{min}}{2\pi}$$

Å thick where $\lambda_{min}$ is the wavelength of light in the optical fiber. The metallic coating can be about 2,800 Å thick.

The system can further include an adhesion layer between the silicon die and the reflective coating. The adhesion layer can include nickel, titanium, or chromium. The adhesion layer can be between 50 Å and 200 Å thick. The adhesion layer can be about 100 Å thick. The interface medium can include an adhesive.

The mirror can be at least 95% reflective, such as at least 98% reflective. The interface medium can be a solid transparent medium. The source of optical radiation can be configured to provide swept-source radiation.

In general, a catheter for use with optical coherence tomography includes an elongate catheter body, an optical fiber in the elongate catheter body, an interface medium, and a mirror in the interface medium. The optical fiber provides a common path for optical radiation reflected from a reference interface and a target. The interface medium is at the reference interface and in optical contact with a distal end of the optical fiber. The mirror includes a silicon die having a reflective coating.

This and other embodiments may include one or more of the following features. The interface medium can include an adhesive. The reflective coating can be metallic. The metallic coating can be gold. The reflective coating can be at least $$\frac{\lambda_{min}}{2\pi}$$

$\lambda_{min}/2\pi$ Å thick where $\lambda_{min}$ is the wavelength of light in the optical fiber. The reflective coating can be about 2,800 Å thick.

The catheter can further include an adhesion layer between the silicon die and the reflective coating. The adhesion layer can be nickel, titanium, or chromium. The adhesion, layer can be between 50 Å and 200 Å thick. The adhesion layer can be about 100 Å thick. The mirror can be at least 95% reflective, such as at least 98% reflective.

In general, a method of performing optical coherence tomography includes transmitting optical radiation from a source through an optical fiber; transmitting the optical radiation from the optical fiber to a mirror embedded in an interface medium, wherein the mirror comprises a silicon die having a reflective coating, and wherein the interface medium is in optical contact with a distal end of a core of the optical fiber; reflecting the optical radiation from the mirror to a target; reflecting the optical radiation from a reference interface, the reference interface between the optical fiber and the interface medium; transmitting optical radiation reflected from the target and reflected from the reference interface along a common path in the optical fiber to a detector; receiving the reflected optical radiation at a detector; and generating an image of the target based upon the reflected optical radiation received by the detector.

This and other embodiments may include one or more of the following features. Transmitting optical radiation can include transmitting swept-source radiation. The reflective coating can be metallic. The metallic coating can be gold. The metallic coating may be at least $$\frac{\lambda_{min}}{2\pi}$$

Å thick where $\lambda_{min}$ is the wavelength of light in the optical fiber. The metallic coating can be about 2,800 Å thick.

The method can further include an adhesion layer between the silicon die and the reflective coating. The adhesion layer can include nickel, titanium, or chromium. The adhesion layer can be between 50 Å and 200 Å thick. The adhesion layer can be about 100 Å thick. The mirror can be at least 95% reflective, such as at least 98% reflective.

In general, a system for optical coherence tomography includes a source of optical radiation, an elongate catheter body, an optical fiber, a handle attached to the proximal end of the elongate catheter body, a detector, and a processor. The optical fiber extends from a proximal end to a distal end of the elongate catheter body and can be attached to a distal end of the catheter body. The optical fiber provides a common path for optical radiation reflected from a reference and a target. The handle is configured to allow rotation of the catheter body and the optical fiber relative to the handle about a longitudinal axis of the elongate catheter body. The detector receives the optical radiation reflected from the reference and the target. The processor generates an image of the target based upon the optical radiation received by the detector.

This and other embodiments may include one or more of the following features. The optical fiber can be attached to the catheter body only near the distal end of the catheter body. A distal end of the optical fiber can be embedded in a solid transparent medium. The optical fiber can be not coaxial with the elongate catheter body. The handle can include a spooling mechanism, and the spooling mechanism can be configured to spool the optical fiber as it rotates. The handle can include a rotating mechanism, wherein one rotation of the rotating mechanism causes the catheter body and optical fiber to rotate about the longitudinal axis more than one time. One rotation of the rotating mechanism can cause the catheter body and optical fiber to rotate about the longitudinal axis at least two times. One rotation of the rotating mechanism can cause the catheter body and optical fiber to rotate about the longitudinal axis about four times.

In general, a catheter for use with optical coherence tomography includes an elongate catheter body, an optical fiber, and a handle. The optical fiber extends from a proximal end to a distal end of the elongate catheter body and is attached to the catheter body near a near a distal end of the catheter body. The optical fiber provides a common path for optical radiation reflected from a reference and a target. The handle is attached to the proximal end of the elongate catheter body and is configured to allow rotation of the catheter body and the optical fiber relative to the handle about a longitudinal axis of the elongate catheter body.

This and other embodiments may include one or more of the following features. The optical fiber can be attached to the catheter body only near the distal end of the catheter body. A distal end of the optical fiber can be embedded in a solid transparent medium. The optical fiber can be not coaxial with the elongate catheter body.

The handle can include a spooling mechanism, the spooling mechanism configured to spool the optical fiber as it rotates. The handle can include a rotating mechanism. One rotation of the rotating mechanism can cause the catheter body and optical fiber to rotate about the longitudinal axis more than one time. One rotation of the rotating mechanism can cause the catheter body and optical fiber to rotate about the longitudinal axis at least two times. One rotation of the rotating mechanism can cause the catheter body and optical fiber to rotate about the longitudinal axis about four times.

In general, a method of conducting optical coherence tomography includes: transmitting optical radiation from a source through an optical fiber, the optical fiber extending from a proximal end to a distal end of an elongate catheter body, the optical fiber attached to the catheter body near a distal end of the catheter body; transmitting the optical radiation from the optical fiber to a first position on a target; transmitting optical radiation reflected from the target and reflected from a reference along a common path in the optical fiber to a detector; receiving the reflected optical radiation at a detector; generating a first image of the first position of the target based upon the reflected optical radiation received by the detector; and manually rotating the catheter body and the optical fiber about a longitudinal axis of the catheter body such that a second image from a second position on the target can be obtained.

This and other embodiments may include one or more of the following features. Transmitting optical radiation can include transmitting swept-source radiation. Rotating the elongate catheter body and the optical fiber can include rotating a distal end of the catheter body and a distal end of the optical fiber together. Rotating the optical fiber can include spooling the optical fiber around a spooling mechanism of a handle attached to the proximal end of the catheter body. Rotating the elongate body and the optical fiber can include rotating a rotating mechanism of a handle attached to the proximal end of the catheter body such that the elongate body and the optical fiber rotate relative to the handle. Rotating the rotating mechanism once can cause the catheter body and optical fiber to rotate about the longitudinal axis more than one time. Rotating the rotating mechanism once can cause the catheter body and the optical fiber to rotate about the longitudinal axis at least two times. Rotating the mechanism once can cause the catheter body and the optical fiber to rotate about the longitudinal axis about four times.

The embodiments described herein may have one or more of the following advantages.

Using an OCT system with a common path optical fiber and an interface medium having indexes of refraction that are mismatched allows the OCT receiving electronics to operate in a total noise range that is within 5 dB of the shot noise limit. Operating within 5 dB of the shot noise limit advantageously ensures that noise in the receiving electronics is low. Keeping noise in the receiving electronics low results in a higher quality image. When used with an atherectomy catheter, for example, higher quality images advantageously allow for better identification of target tissue.

Using swept source optical radiation and a common path optical fiber as part of an OCT system allows for the use of a significantly simplified optical system compared to standard time-domain OCT embodiments or swept-source embodiments using Michaelson or Mach-Zehnder interferometers. This allows for the most efficient use of optical radiation, which in turn permits well optimized detection of signal and commensurately higher image quality.

Embedding a silicon die having a reflective coating in an interface medium provides a high reflectivity surface for reflection of light from the fiber to the tissue and back from the tissue into the fiber. The high reflectivity surface ensures that a high percentage of light from the source of optical radiation will be reflected and returned from the tissue. Having more light reflected from the target improves the interference fringe contrast, resulting in a higher quality image.

A system for OCT that includes a common path optical fiber attached to a distal end of the catheter body and a handle attached to the proximal end of the elongate catheter body to rotate the catheter and the optical fiber allows the optical fiber to rotate with the catheter body without breaking or stretching. Allowing the optical fiber to rotate with the catheter body ensures that images can be taken at 360° angles about the catheter body. Taking images at 360° angles around the catheter body ensures that more tissue can be imaged. Moreover, including an optical fiber attached to a distal end of the catheter body and a handle attached to the proximal end of the elongate body to rotate the catheter and the optical fiber advantageously avoids having an additional bulky mechanism to rotate the fiber independently of the catheter.

These and other advantages will be apparent from the following description and claims.

BRIEF DESCRIPTION OF THE DRAWINGS

FIG. 3C shows a chart including data drawn from the graphs in FIGS. 3A and 3B.

DETAILED DESCRIPTION OF THE INVENTION

The Optical Coherence Tomography (OCT) catheters and systems described herein are configured to provide image guided intra-vascular procedures that may be particularly useful for the diagnosis and/or treatment of arterial disease. The systems may include a catheter, an umbilical connection, and a console. The system uses OCT to form an image of the intravascular environment close to the catheter cutter. FIG. 2B shows a schematic of one variations of an OCT system described in greater detail herein.

During intraluminal procedures, such as atherectomy, problems can arise as a result of failure to properly identify target tissue. By using a catheter having a common path optical fiber for OCT, proper identification of target tissue can be improved.

Figure 1:
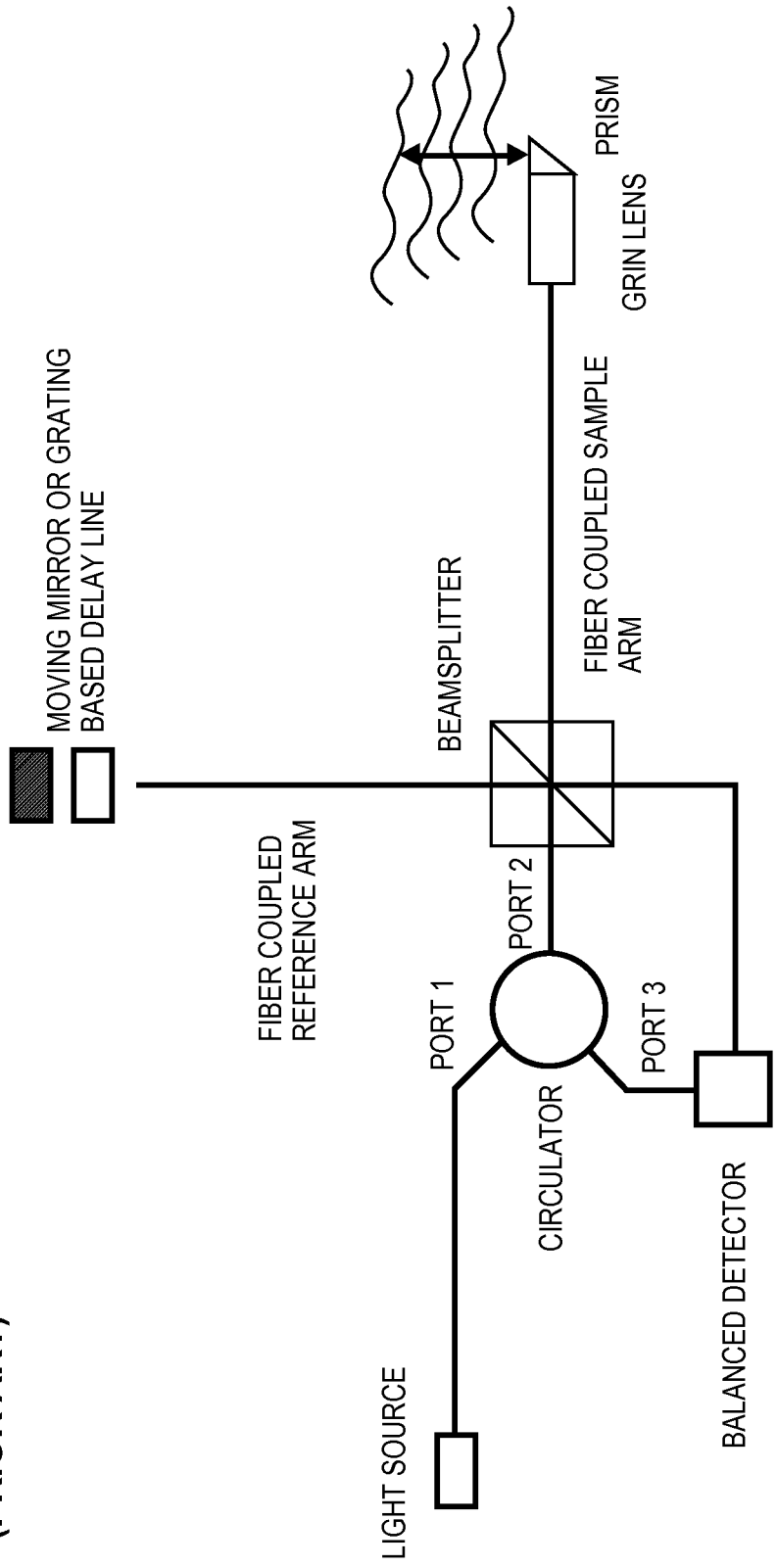
FIG. 1 shows an example of a prior art OCT system.
Figure 2A:
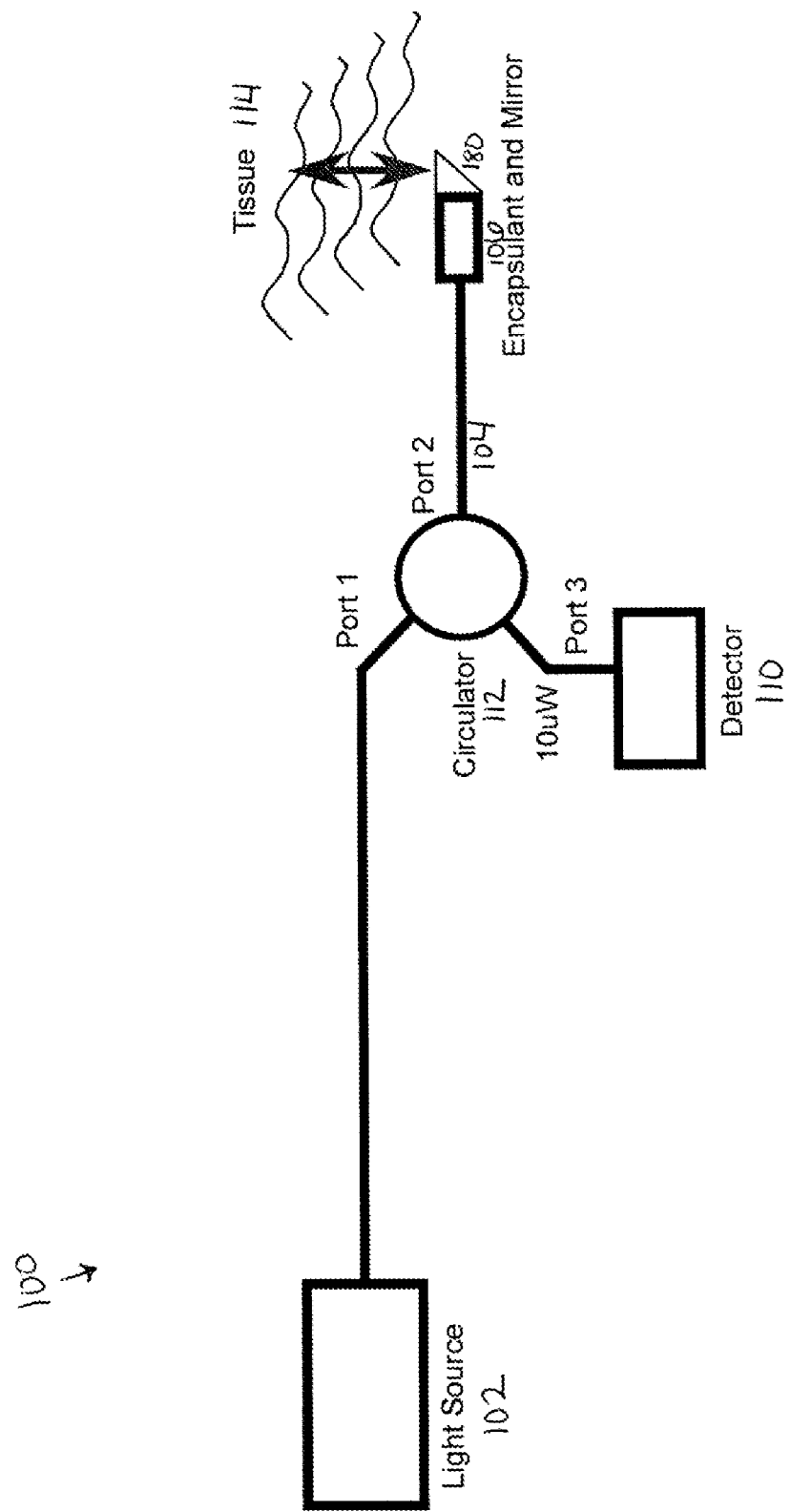
FIG. 2A shows an exemplary OCT system as described herein.
Figure 2B:
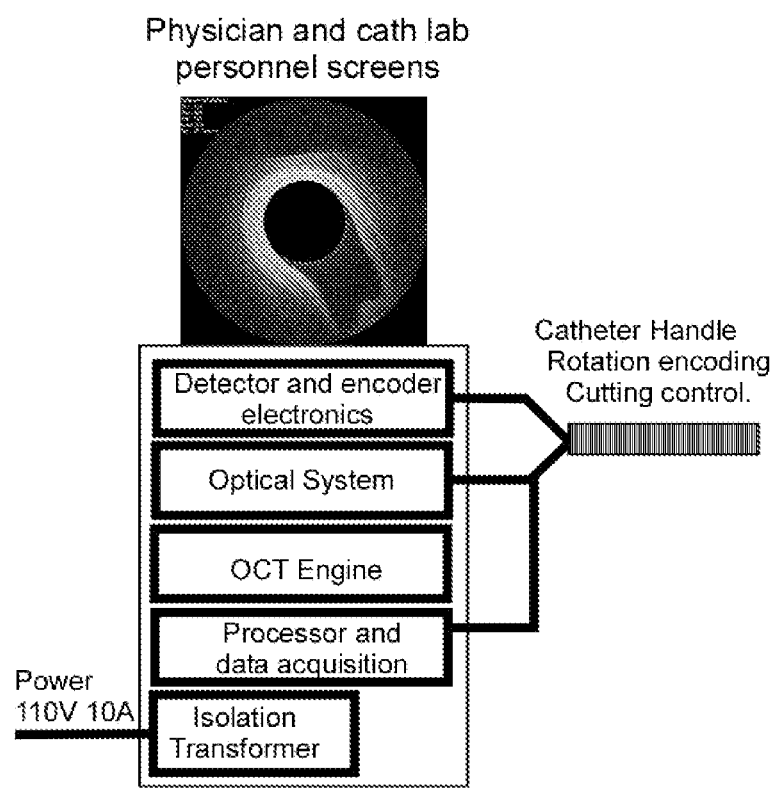
FIG. 2B is a schematic illustration of an OCT system as described herein.

Referring to FIG. 2, a common-path OCT system 100 includes a laser source 102, such as a swept frequency light source. An optical fiber 104 transfers radiation from the laser source 102 to the target 114. The optical fiber 104 is in optical contact with an interface medium 106, i.e. the light exiting the optical fiber and entering the interface medium sees only one interface. In some embodiments, as shown in FIG. 2, the end of the optical fiber is embedded in the interface medium 106.

In the common-path OCT system 100, the index of refraction of the interface medium 106 is different than the index of refraction of the core of the optical fiber 104. This creates a Fresnel reflection, in which part of the light exits the core, and part of the light is reflected back. Some of the light beam that exits the optical fiber 104 will encounter the target 114 and be reflected or scattered by the target 114. Some of this reflected or scattered light will, in turn, reenter the tip of the optical fiber 104 and travel back down the fiber 104 in the opposite direction. A Faraday isolation device 112, such as a Faraday Effect optical circulator, can be used to separate the paths of the outgoing light source signal and the target and reference signals returning from the distal end of the fiber. The reflected or scattered target light and the Fresnel-reflected reference light from the fiber face can travel back to a detector 110 located at the proximal end of the optical fiber 104.

Because the reflected or scattered target light in the OCT system 100 travels a longer distance than the Fresnel reflected reference light, the reflected or scattered target light can be displaced by frequency, phase and or time with respect to the reference beam. For example, if swept-source radiation is used, then the light from the target will be displaced in frequency. The difference in displacement in phase, time or frequency between the reflected or scattered target light and the reference light can be used to derive the path length difference between the end of the optical fiber tip and the light reflecting or light scattering region of the target. In the case of swept source OCT, the displacement is encoded as a beat frequency heterodyned on the carrier reference beam. Embodiments of the above concept where the light paths in the reference and signal arms are common are called common path interferometers. Common path interferometry satisfies the requirements of a low cost disposable device, as it eliminates the separate reference arm but places no additional burden on the catheter construction.

The laser source 102 can operate at a wavelength within the biological window where both hemoglobin and water do not strongly absorb the light, i.e. between 800 nm and 1.4 μm. For example, the laser source 102 can operate at a center wavelength of between about 1300 nm and 1400 nm, such as about 1310 nm to 1340 nm. The optical fiber 104 can be a single mode optical fiber for the ranges of wavelengths provided by the laser source 102.

The core of the optical fiber 104 and the interface medium 106 can have specifically-chosen indexes of reflection such that a known magnitude of Fresnel reflection is created. For example, the indexes of reflection can be chosen such that noise in the OCT system is minimized.

Noise in OCT systems comes from at least three sources: shot noise, thermal or Johnson noise, and residual intensity noise (RIN noise). There may additionally be noise from the analog-to-digital conversion process. RIN noise comes from noise intrinsic to the light source, tends to dominate at high reference powers, and can be limited by limiting the maximum laser light intensity, working with an alternative low RIN light source (non-laser), or by using balanced detection. Thermal (Johnson) noise tends to dominate at low reference power levels, and can be avoided by working at reference power levels yielding a DC photodiode current above that of the thermal noise floor.

Shot noise dominates in between RIN noise and thermal (Johnson) noise. Shot noise is caused by statistical fluctuations in the number of photons or electrons that carry a particular signal. For a well designed system, shot noise is the limiting factor in dynamic range. The indexes of refraction of the fiber 104 and the interface medium 106 can thus be chosen such that the OCT system 100 operates close to the shot noise limit.

Figure 3A:
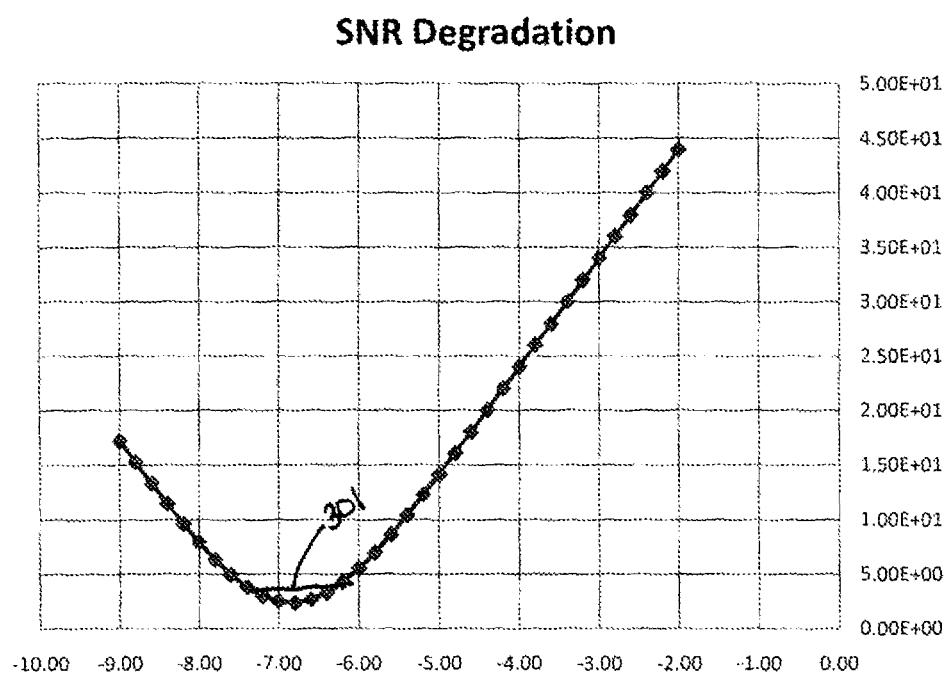
FIG. 3A shows an exemplary graph of noise in an OCT detector vs. power.

The shot noise limit of a particular receiver is set by the responsivity of the photodetector, the detection bandwidth desired, and the reference DC power impinging on the detector element. An exemplary graph of a noise v. power is shown in FIG. 3A with a break-down by the type of noise shown in FIG. 3B. The graphs in FIGS. 3A and 3B assume a system having 10 mW of forward power, 1550 nm center wavelength, 20 nm bandwidth, 1 MHz detection bandwidth, and a 1A/W responsivity.

The shot noise limit is the area 301 at the bottom of the curve in FIG. 3A, at which the noise is the lowest or where the degradation from the shot noise limit is the least. Using the graph for a particular receiver, such as the graphs shown in FIG. 3A and FIG. 3B, the desired power at the detector, $P_{det}$, can be determined that would place the noise within a desired range of the shot noise limit. For example, FIG. 3C shows a table of values drawn from FIG. 3B. Referring to FIG. 3C, a power of 0.158 μW would place the receiver at the minimum degradation point, 2.36 dB above the shot noise limit. Moreover, reference powers of between 63.1 nW and 251 nW would place the noise within 3 dB of the shot noise limit. Reference powers of between about 25 nW to 0.631µW would place the noise within 5 dB of the shot noise limit.

To determine the total power, $P_{out}$, that must be reflected from the interface 106 to obtain the desired $P_{det}$, the losses of the detector 110 must be taken into account according to Equation 1:

$$P_{det} = P_{out}(1-L) \qquad \text{(equation 1)}$$

where $P_{out}$ is the power reflected from the reference interface, and L is the sum of the optical losses from the distal end of the probe to the detector 110. Therefore, assuming that $P_{det}$ is equal to 0.2µW (rounding from the 0.158 µW determined to place the noise as low to the shot noise limit as possible) and that the intermediate optical system operates at 90% efficiency such that L is 10%, $P_{out}$ is equal to 0.4 W/(0.9)=0.222 µW.

The forward power at the distal end of the optical fiber prior to entering the interface medium is given by $P_{in}$. Therefore, assume that that $P_{in}$ is equal to 10 mW.

Moreover, $P_{out}$ and $P_{in}$, can be used to determine the reflectivity of the reference interface 180, according to equation 3:

$$P_{out} = P_{in} r^2 \qquad \text{(equation 3)}$$

where r is the Fresnel coefficient of reflectivity. Therefore, assuming that $P_{out}$ is 0.222 µW, and $P_{in}$ is 10 mW, as solved for via equations 2 and 3, then r is equivalent to 0.004714.

Moreover, the Fresnel equation (shown by equation 4) governs the intensity of reflection from a normal or near normal interface:

$$r = \left(\frac{n_1 - n_2}{n_1 + n_2}\right) \qquad \text{(equation 4)}$$

where the index of refraction of the transparent medium is given by $n_2$ and that of the core is $n_1$.

The index of refraction of the core of the optical fiber, $n_1$, is fixed by the manufacturer, and varies depending upon the fiber. The optical fiber can be, for example, a Corning SMF-28e, Corning ClearCurve, OFS BF05717 and EZBend, Fujikura SR-15e with enhanced band loss resistance, Draka BendBright XS and BendBright Elite. For Corning SMF-28e, the group refractive index of the core at 1.3 microns is 1.4677. By comparison, a Fujikura ImageFiber has $n_1 = \sim 1.500$.

Therefore, assuming that |r| is 0.004714 as solved for with respect to equation 3 and that $n_1$, is 1.4677, the index of refraction of the interface medium $n_2$ should be approximately 1.4816 or 1.4539. Thus, an interface medium of either index will produce the desired reference reflection. In some embodiments, the medium with the higher index of refraction may be preferable as it may be more readily available and/or have better mechanical properties, such as tensile strength.

The interface medium used with system 100 can be, for example, an adhesive. Depending upon the required index of refraction, the interface medium can be, for example, M21-CL which is a thermal curing adhesive. Another exemplary interface medium is the Light Weld® UV curable photonics adhesive OP-4-20658, produced by Dymax corporation, Torrington Conn. This adhesive, which has a refractive index of 1.585 in the cured state, is a rigid clear UV-curable adhesive that can be applied in a liquid form, and which then cures to a rigid form within seconds of exposure to UV light. Another exemplary transparent medium is EpoTek 0G127-4 or 0G116, produced by Epoxy Technology, Billerica Mass. This has a refractive index of 1.602 in the cured state.

If an interface medium having the exact refractive index desired cannot be found (for example because it does not have the proper tensile strength or is not biocompatible), an interface medium having a refractive index that is close can be selected and the power in, $P_{in}$, can be adjusted accordingly. Using the known r and the desired power at the detector, $P_{det}$, the required power in $P_i$, can then be determined according to equation 5:

$$P_{det} = P_{in} r^2 (1-L) \qquad \text{(equation 5)}$$

In some implementations, the interface medium can be applied in a semi-liquid state, such as by dispenser, ink jet deposition, spraying, painting, dipping, or other process. The medium may then be cured to a solid form, such as by UV curing, thermal curing, chemical curing, drying, or other process. Other processes, such as vacuum deposition of transparent medium or direct mechanical placement of the transparent medium may also be used.

The interface medium can have a minimum thickness (i.e. depth between the end of the optical fiber and the end of the interface medium) of at least $$\frac{\lambda_{min}}{2\pi},$$

where $\lambda_{min}$ is the wavelength of light in the optical fiber. For a wavelength of over 1250 nm, this will be approximately 200 nm or greater. The interface medium can also have a thickness that is great enough to introduce an offset between the reference reflection and the minimum distance that the target can approach the distal exit face of the fiber.

Figure 4A:
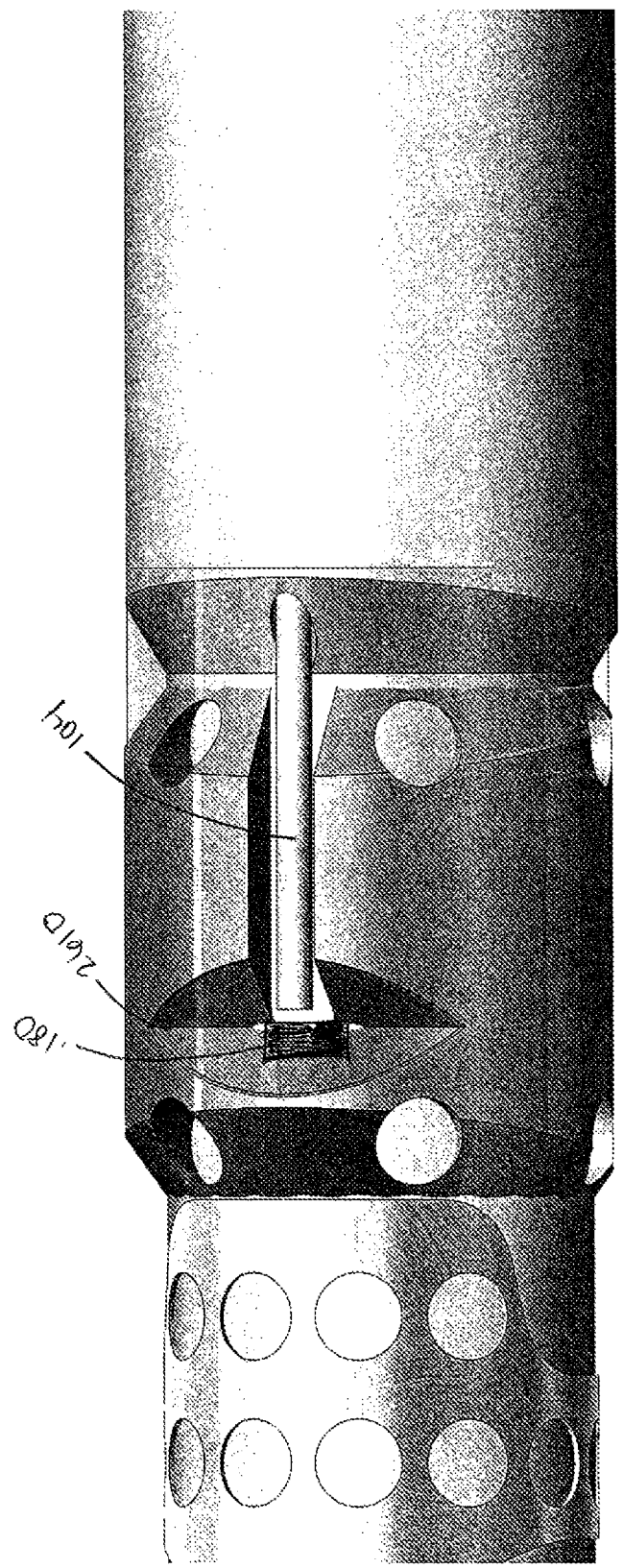
FIG. 4A is a top view of an exemplary mirror at the distal tip of an OCT catheter.
Figure 4B:
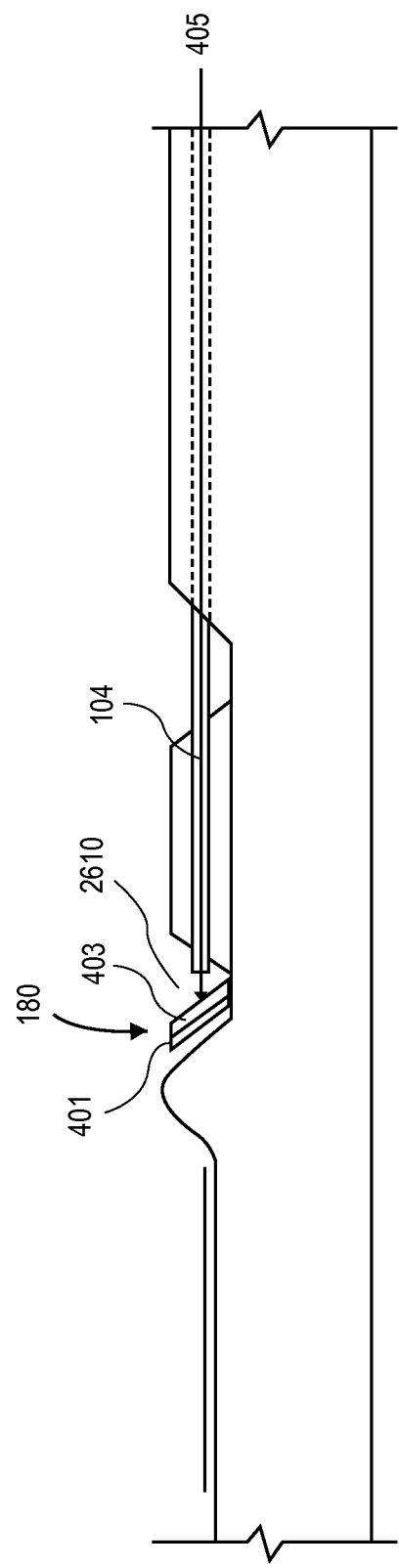
FIG. 4B is a cross-sectional side view the embodiment of FIG. 4A.

Referring back to FIG. 2 and to FIGS. 4A and 4B, the mirror 180 must be properly designed and optimized in order to fit into the small (approximately 2 mm) diameter of the catheter head and to reflect into a blood vessel tissue located up to 1-3 mm away from the side of the distal catheter tip. As shown in FIG. 4B, the mirror 180 can include a silicon die 401 having a reflective coating 403. The reflective coating 403 can be, for example, a gold coating. The reflective coating 403 can be greater than $$\frac{\lambda_{min}}{2\pi},$$

where $\lambda_{min}$ is the wavelength of light in the optical fiber. For example, the metallic coating can be greater than about 2,800 Å thick.

Further, the surface of the silicon die 401 under the reflective coating 403 can be polished to less than 400 nm peak-to-peak roughness, such as better than 300 nm peak-to-peak roughness, for example about 200 nm peak-to-peak roughness. An adhesive, such as nickel, titanium, or chromium, can be used to adhere the gold coating to the silicon die. The adhesive can be between about 50 Å and 200 Å thick, such as about 100 Å thick. The mirror 180 of this configuration can be at least 95% reflective, such as 98% reflective.

The mirror 180 can be placed on a slope such that it is at an angle of between 30° and 60°, such as 45° with respect to a longitudinal axis 405 of the core of the optical fiber 104.

Moreover, the mirror 180 can be configured such that the total distance that the light travels from the fiber 104 to the mirror 180 and out to the sample is between 100 and 400 µm, such as between 200 and 250 µm.

Figure 3B:
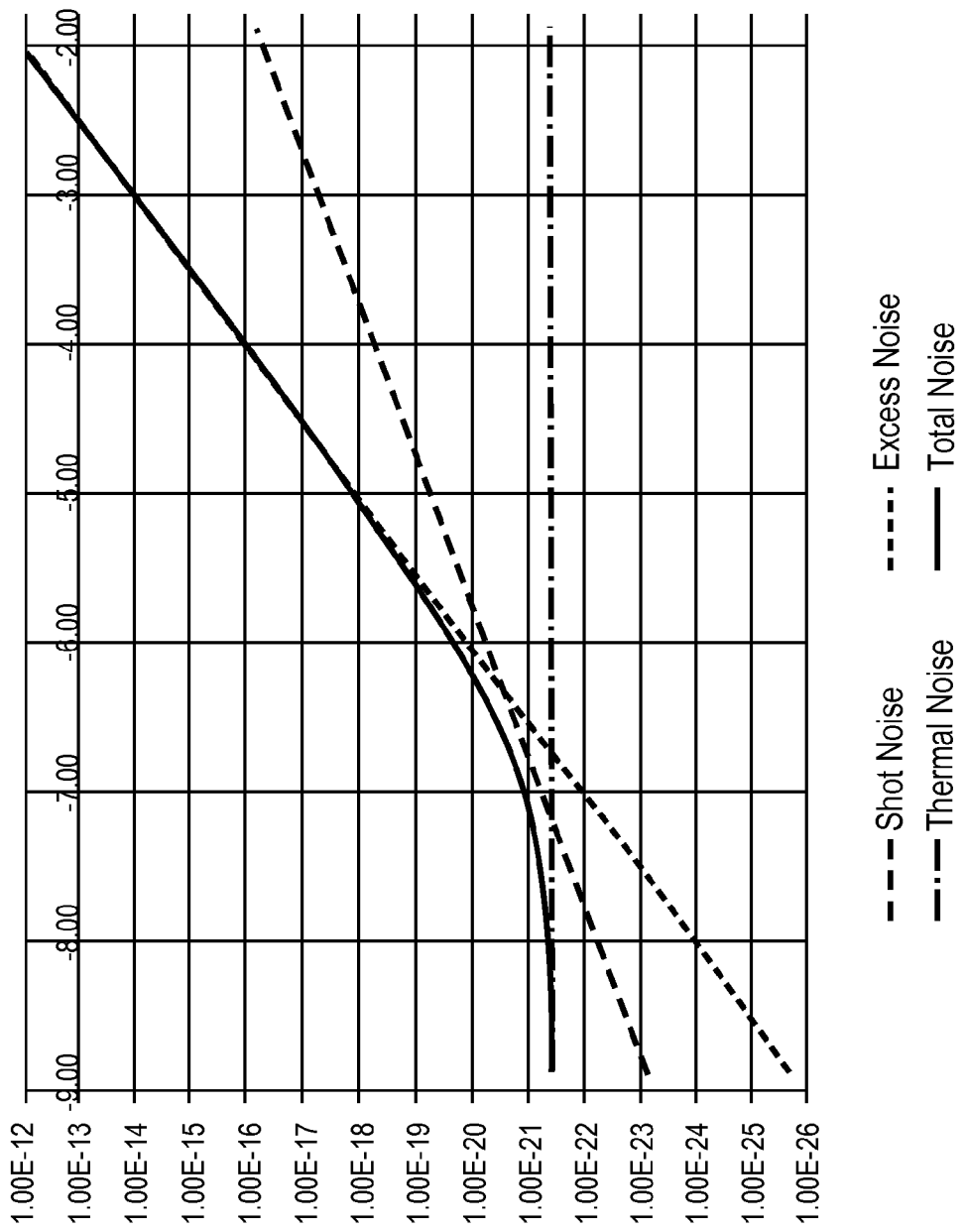
FIG. 3B shows an exemplary graph of a breakdown of the types of noise contributing to the total noise in the graph of FIG. 3A.

As shown in FIGS. 3A and 3B, the imaging system described herein can be used with a catheter, such as an atherectomy catheter 502. An opening 2610 can be formed in the catheter 502, exposing the distal end of the fiber 104. The OCT mirror 180 can be placed in the opening near the distal tip of the catheter 104, and the interface medium can cover or embed the fiber 502, groove 2608, and opening 2610.

Figure 5:
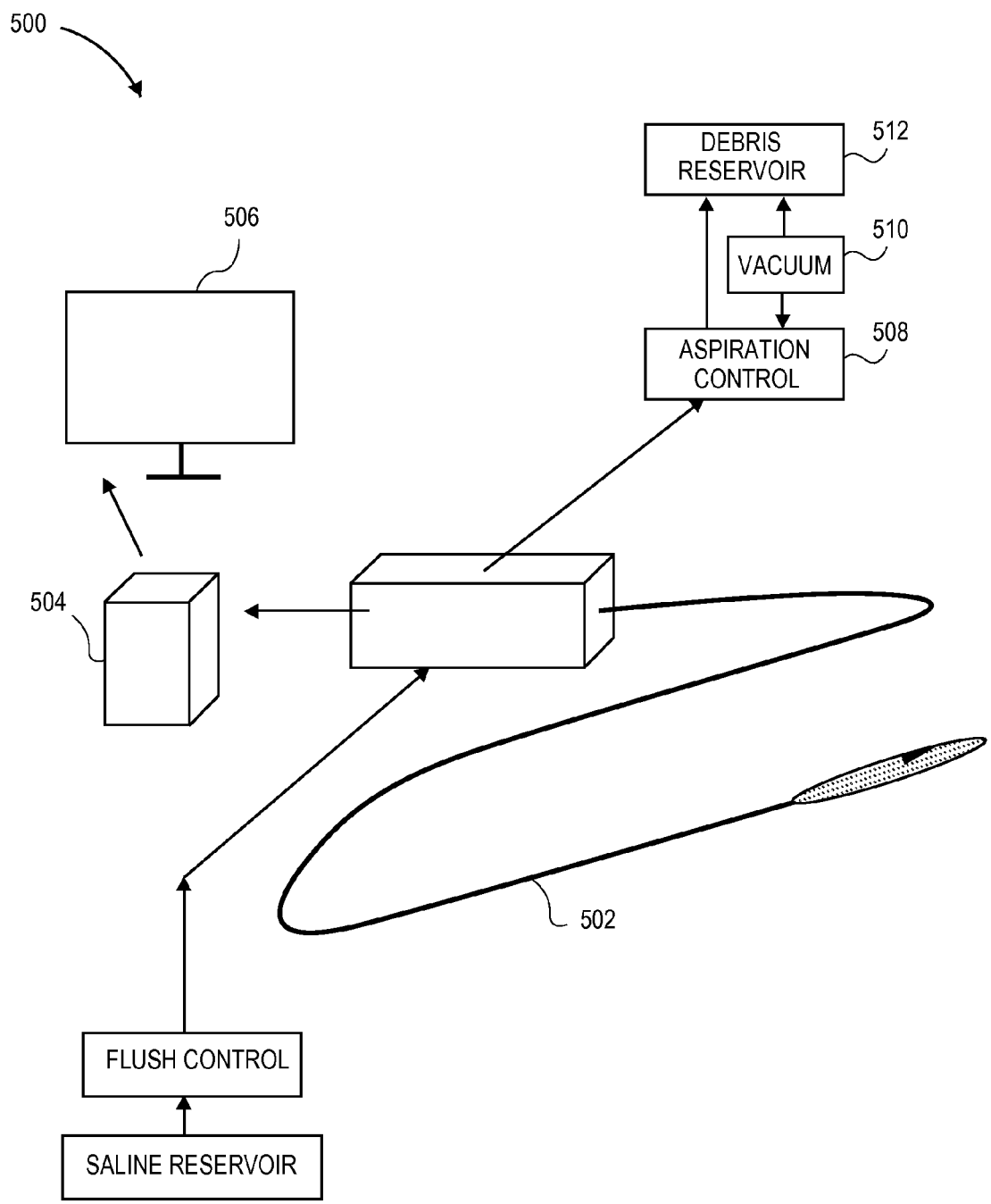
FIG. 5 shows a medical (cardiovascular) catheter system equipped with an OCT system.

FIG. 5 shows an overview of the main components of an OCT imaging system 500 including a fiber optic catheter 502. The catheter 502 can be sized to fit into a blood vessel, e.g. can be about 2 mm in diameter. In this configuration, the OCT optical apparatus 504 (including the light source, optical circulator, and detectors) can be located at the proximal end of the catheter 502, and can be connected to an image processor and a display 506. The distal end of the catheter 502 includes the image fiber and the mirror. The system 500 is designed to be used within the body of a patient for various medical purposes, such as atherectomy. Thus, other components, such as a vacuum 510, aspiration control 508, and a debris reservoir 512 may be useful.

The system described herein may be used to produce relatively narrow angle images of a portion of an interior lumen of a human body, such as the interior of a blood vessel. Looking at a section of a tissue through a single OCT optical fiber is limited in that the useful angle of view produced by a single OCT optical fiber is at most a few degrees. In order to produce a more medically useful panoramic view of a wide arc or swath from the interior of a blood vessel, such as 45°, 90°, 120°, or more, the catheter containing the optical fiber can be rotated.

Figure 6A:
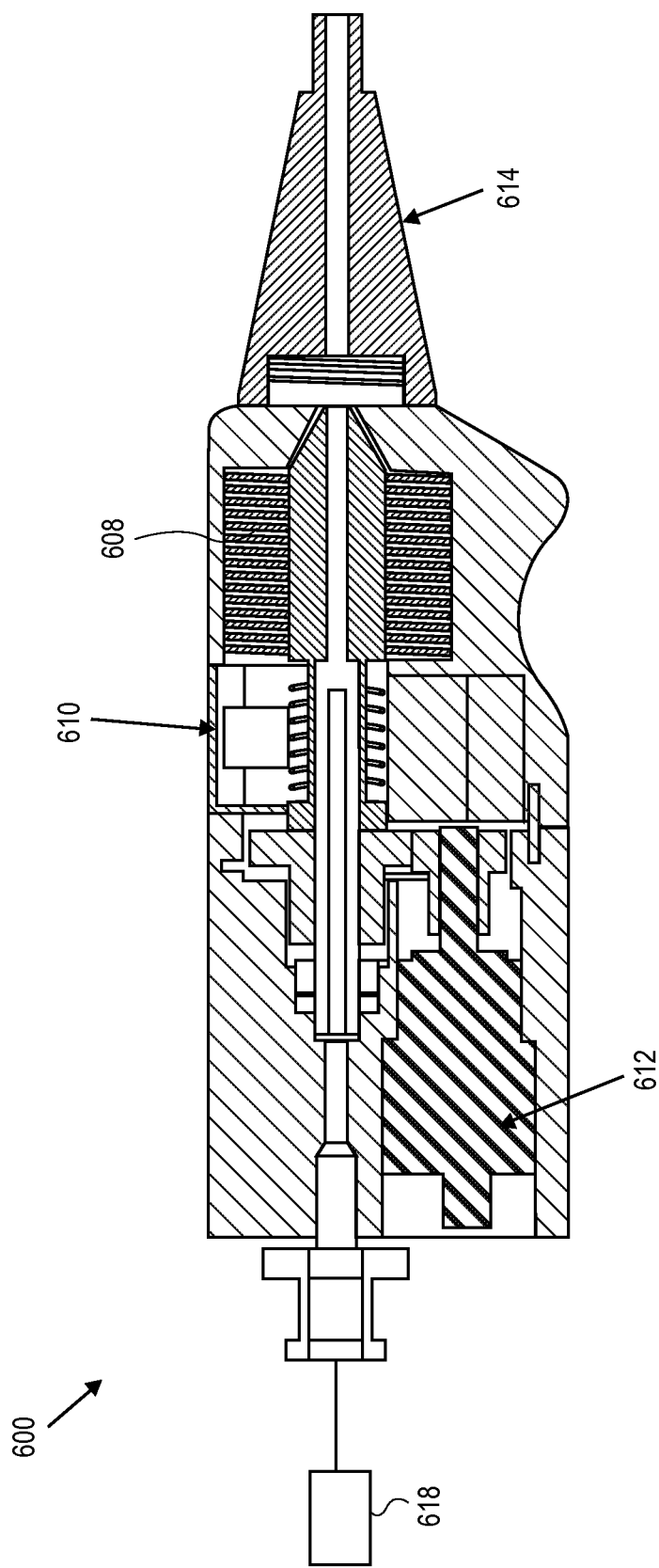
FIGS. 6A and 6B show an exemplary embodiment of a fiber uptake system.
Figure 6B:
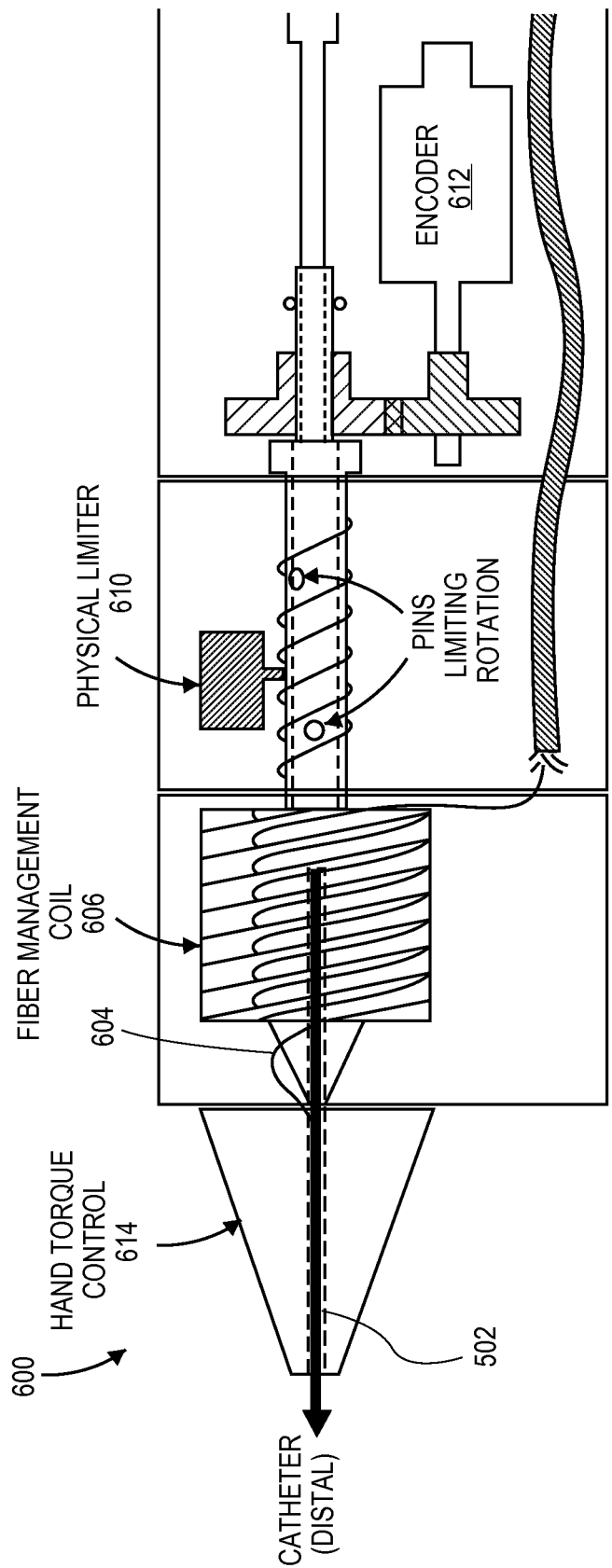

Referring to FIGS. 6A and 6B, the catheter 502 can be attached to a fiber uptake system 600. The optical fiber 604 can extend through the catheter 502 and can be attached at the distal end of the catheter 502. The fiber 604 can otherwise be allowed to float freely through the catheter 502, e.g., can be attached only at the distal end of the catheter 502. Doing so prevents build up of optical losses due to microbending or stress-induced birefringence. Further, the fiber 604 can be located off the central longitudinal axis of the catheter 502.

The fiber management system 600 incorporates the fiber on a single internal take-up spool 606. The take-up spool is configured with grooves 608 (see FIG. 6A) sized to fit the optical fiber 604. The optical fiber 608 can move up and down in the grooves 608 (i.e. radially with respect to the catheter 502) to compensate for any bending or stretching of the catheter 502.

The uptake system 600 further includes a physical limiter 610 configured to prohibit the take-up spool from rotating further than the OCT fiber 602 is configured to stretch. Moreover, a torque control knob 614 can be attached to the proximal end of the catheter 502. The knob 614 can be used to actuate rotation of the catheter, and thus rotation of the fiber 604. For example, the knob 614 can be manually activated. The knob 614 can also be motor-driven by a proximal controller 618 to provide a more controlled sector sweep of the imaging element. The knob 614 can be configured such that one rotation of the knob 614 causes the catheter 502 and optical fiber 604 to rotate more than once. For example, the optical fiber 604 can rotate about the longitudinal axis at least two times, such as about four times for every single rotation of the catheter 502.

An encoder 612 in the uptake system 600 detects angle and constantly relays information regarding rotation of the fiber 604 back to the computer controlling the OCT data acquisition system. This value of the angle is incorporated into the display algorithm so as to show a 360 degree view of the inside of the lumen.

Rather than having an encoder 612, the controller 618 can include a "mouse chip" position sensor similar to those used in a computer optical mouse in order to look at the catheter and encode angular and longitudinal motion. The mouse chip can be configured to look at the surface of the catheter (or the braid if the outside laminate is transparent or translucent) and calculate the X and Y motion vectors on the basis of the difference in feature position between adjacent snapshots.

Rotating the proximal end of the catheter by, 360° does not necessarily lead to a 360° rotation at the distal tip, particularly if the catheter is experiencing distributed friction over its length, for example from the introducer sheath, guides, tissue friction especially in a tight lesion. By using a mouse chip, rotation and longitudinal motion of the catheter can be detected while eliminating the unsupported length effect.

Figure 7:
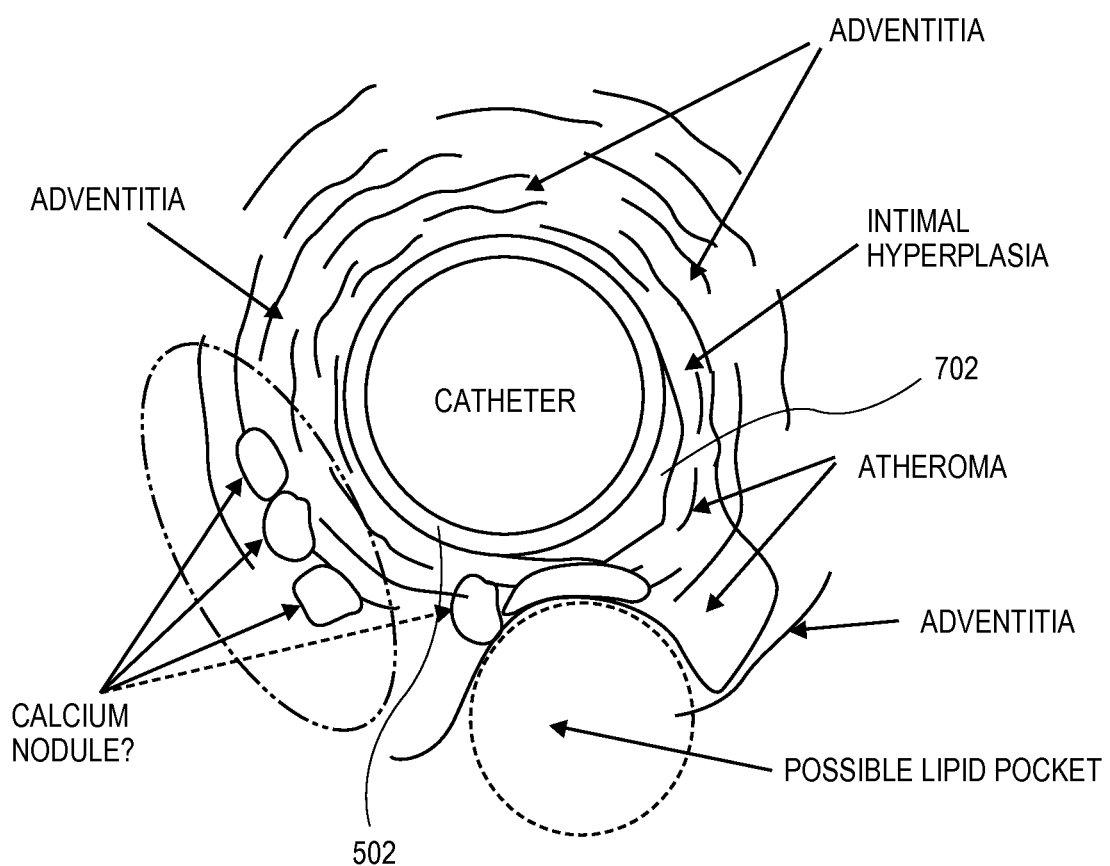
FIG. 7 shows an exemplary OCT image from an OCT system.

An exemplary image or display of a catheter 502 in a lumen 702 is shown in FIG. 7. The display can be continually refreshed by rotating the catheter in either direction. The whole display can also be rotated and oriented with respect to the fluoroscopic view being acquired simultaneously in the cath lab using X-ray. For example, the image may be rotated so that the pericardium is "Up" or "Down". By orienting the display and knowing the spatial relationship between the catheter and the display (and by implication the critical physiological structures in the vessel), the physician may orient the device as required, e.g. to cut an occlusion properly.

The OCT system 100 described herein can produce images, e.g. images of tissue morphology, having a resolution of around 6-15 microns, e.g. 8-10 microns, and to depths of 1-2 mm depending on the optical properties of the sample being imaged. The axial resolution of the OCT system can be about ten times higher than that of a similar ultrasound system.

Figure 8:
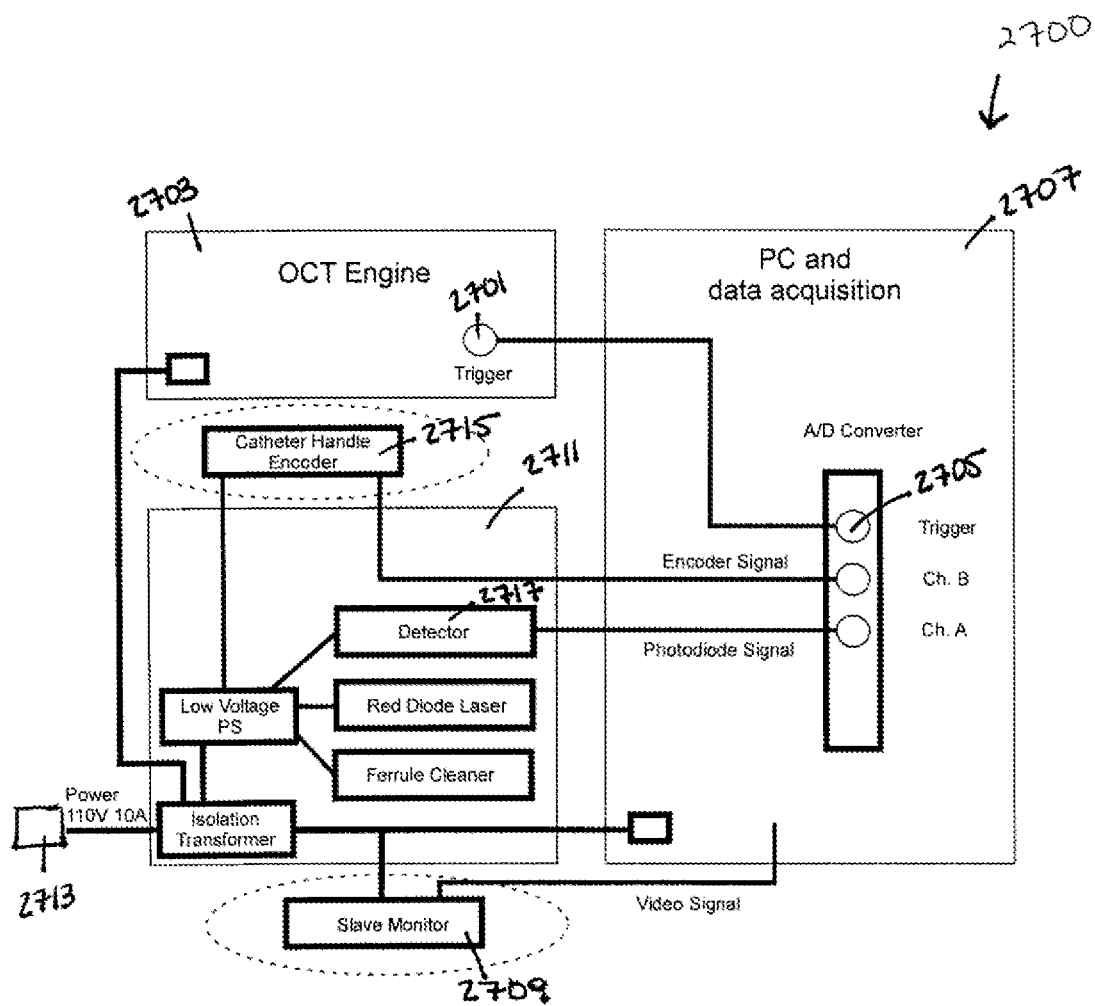
FIG. 8 shows a system for implementing the OCT system and catheter.

FIG. 8 shows a system 2700 for implementing the OCT system and catheter described herein. A power supply 2713 supplies power to the OCT engine 2703, the computer processor 2707, and the optical system 2711. A trigger 2701 in the OCT engine 2703 is connected to a trigger 2705 in the computer processor 2707 to begin processing of the image. Moreover, the catheter handle encoder 2715 is attached to the computer processor 2707 to transfer signals related to the location and rotation of the optic fiber. The OCT detector 2717 is attached to the computer processor 2707 to process the final image. Finally, a video signal is sent from the computer processor 2707 to a monitor 2709 to output the image to the user.

In some embodiments, the OCT system and catheter described herein can image up to 1-2 mm in depth with resolutions around 8-10 microns, sufficient to give the physician highly detailed images almost to the cellular organization level and visibility beyond the maximum cut range of the catheter. Moreover, the OCT atherectomy catheter described in can advantageously have imaging capability with crossing-profile impact that is much smaller than traditional OCT systems and ultrasound transducers.

EXAMPLE

In one example, an image-guided interventional catheter (e.g., an OCT catheter as described above) may be used to address unmet needs in peripheral and coronary artery disease (atherosclerosis). The system may include a console having a modest footprint and in a cath lab without need for extensive integration into cath lab systems. In some variations, the systems described herein may be integrated with other catheter (e.g., guidance, control, imaging) systems. The system may be configured to allow a procedure to start/proceed/finish under fluoro guidance in the event of a system failure. The system is also configured to be compatible with sterile procedures.

As mentioned above, the OCT systems described herein may allow real-time information on intravascular lesion morphology and device orientation in the vessel. This and other features may also allow improved navigation precision around complex anatomy (e.g., bifurcations, ostials, tortuosity, cutting on a curve, etc.), and around stent struts. The catheters may be safely used to traverse diseased tissue while reducing incidence of perforations and dissections potentially associated with a more aggressive treatment strategy. The systems may also provide immediate assessment of acute procedural success, and a reduction in procedure time compared to contemporary interventional techniques. The systems described herein may allow imaging of vessel wall morphology in real time and at a level of precision that could assist the physician in making a "diseased/not-diseased" determination.

In one example, the OCT system is configured to allow tissue morphology to be imaged in real time with resolution routinely around 8-10 microns, and to depths of 1-2 mm depending on the optical properties of the tissue. The axial resolution of OCT is sufficiently high that the images presented to the operator substantially resemble histology from optical microscopy, and are as a result more intuitively interpreted than ultrasound or MRI/CT images. The depth to which OCT can image through tissue with minimal to moderate lipid content is sufficient to give the physician visibility beyond the maximum proposed depth of cut for an atherectomy catheter, allowing the safety margins of the putative cut to be assessed.

As mentioned, OCT has several other technical and economic advantages for catheter applications. The impact on catheter crossing profile of the OCT optical fiber is much smaller than for even the smallest comparable ultrasound transducer. The axial resolution of OCT is typically 10× higher than ultrasound; this translates directly to image interpretability. The limited depth of penetration of typical OCT devices is not of primary concern in this application in many applications, because it is known from prior atherectomy procedures that substantial clinical benefit can be obtained by removing several hundred micron thicknesses of tissue. The depth of penetration may be matched to the expected maximum cut depth. Regions of particularly deep or thick tissue (target tissue to be removed) may be identified and treated serially or separately. For example, highly lipid-rich tissues (necrotic cores) appear as dark voids in OCT images, typically with bright caps.

The center wavelength for the optical system may be chosen to provide sufficient depth of penetration, as well as compatibility with the components of the system. For example, the OCT systems may use light that can be transmitted through fused silica fiber optics (where the primary investment in cost and quality has been made). The wavelength range to 250-2000 nm may be particularly useful. Single mode fibers can be readily obtained at any of these wavelength ranges, although wavelengths above 400 nm may be preferable. Other wavelengths could be used, but there may be significant toxicity issues with fiber materials transmitting further into the infrared, and optical sources with the appropriate properties may be difficult to obtain. Below 250 nm air-guiding fibers may be used, however these may be less desirable. In this example, we assume a range of between about 250-2000 nm.

It may be easier to "see" through small annuli of either blood, saline or mixtures by restricting the scan range of the source to regions where hemoglobin and water do not strongly absorb light. This leads to the use of a "biological window" between about 800 nm and 1.4 microns.

The dominant mechanism restricting penetration depth in biological tissue when using ballistic optical scattering techniques is the photon scattering cross-section in the tissue. Higher scattering cross-sections causes fewer photons to traverse from source to target and back ballistically, that is with only one scattering event at the target leading to a reduction in useful signal. The scattering cross-section scales as an inverse power of wavelength over the 250-2000 nm range, transitioning from an exponent of −4 at shorter wavelengths to a smaller value at longer wavelengths. The value decreases monotonically going from short to longer wavelengths so, if our need is to see deeper in tissue, the wavelength range of the source should be biased to longer wavelengths. However, this choice is not without compromise. Moving to longer wavelengths may require a more sophisticated laser source to achieve the same resolution compared to imaging at shorter wavelengths, however this is a soluble technical problem.

In some variations the system takes advantage of the widespread availability of cheap, high quality parts. For example, fiber-based telecommunications has evolved at three specific center wavelength ranges; 800 (LAN only), 1310 (O-band) and 1550 nm (C-band). The systems described herein may restrict the choice of center wavelength to 1310 nm, however this does not mean that the other two wavelength ranges could not be made to work. For example, the 800 nm center wavelength range is routinely used in opthalmology, where depth of penetration can be sacrificed for tissue layer resolution and where fiber delivery is not a requirement (free-space optics may be used).

In some variations, the system works in the telecommunications O-band. In practice the range of center wavelength is 1315-1340 nm may be dictated by the availability of suitable laser sources in the O-band.

There are three primary categories of source/detector combinations in OCT, namely Time-Domain, Spectral-Domain (Fourier Domain or Spectral Radar) and Swept Source OCT. The examples of OCT systems described herein are swept source OCT (SS-OCT), which allow for video-rate imaging, few or no moving parts, a simple optical system suitable for fiber implementation, imaging to depths greater than 1 mm, and insensitivity to the rigors of a mobile environment.

As discussed above, several interferometer configurations may be used. The systems described herein are Common Path Interferometry (CPI) systems. This has several advantages given the goal of catheter based imaging with cost-constrained capital equipment and disposable devices. The SS-OCT with CPI system described herein preserves the Fellgett Advantage. Fellgett's advantage or the multiplex advantage is an improvement in spectroscopic techniques that is gained when an interferometer is used instead of a monochromator or scanning delay line. The improvement arises because when an interferometer is employed, the radiation that would otherwise be partially or wholly rejected by the monochromator or scanning delay line in its path retains its original intensity. This results in greater efficiency. This embodiment contrasts this with the other systems, in which only a small fraction of the laser power is useful at any given time. For example, the Lightlab™ M2 system uses TD-OCT with a scanning delay line, which is equivalent for the purposes of the Fellgett Advantage to a monochromator. Clinically, the Fellgett advantage impacts imaging speed (frame update rate), allowing significant improvements in video display rates which translate to a reduction in ambiguity in interpreting the image.

The CPI systems described herein also preserve the Jacquinot Advantage. The Jacquinot advantage states that in a lossless optical system, the brightness of the object equals the brightness of the image. Assuming that losses due the optical components are negligible, an interferometer's output will be nearly equal in intensity to the input intensity, thus making it easier to detect the signal. This translates directly to image quality, and a more interpretable image.

The CPI system as described herein therefore makes highly efficient use of the laser power. Light is either used for the reference reflection or impinges on the tissue and is used to create signal. No light is lost in attenuators or additional optical components or unused reciprocal paths. This efficient use of laser power is most apparent in the ability of the system to display clinically relevant images of the intravascular environment in real time, without the need for extensive post processing or even on-the-fly image correction.

Furthermore, these systems are "down-lead insensitive", allowing the connection from catheter to console to be of almost arbitrary length without forcing a matched reference delay line to be shipped with each catheter. This minimizes the additional cost impact of the imaging components added to the catheter. It also allows a console component to be positioned almost anywhere, minimizing the potential disruption to work flow and minimizing the threat to a sterile field.

The systems described herein also minimize the number of optical components in the imaging system which could contribute to chromatic aberration. This minimization preserves the spectral fidelity of the laser source optimizing the layer resolution. This translates directly to image quality, and a more interpretable image.

The common-path systems described herein also have exceptional phase stability. Path length changes affecting the sample arm (temperature changes, stress-induced birefringence etc) also affect the reference arm identically. The distance from the ZPD (zero-pathlength difference) point (the reference plane) to the sample is physically fixed and is not subject to variability due to turbulence. This exceptional phase stability coupled with the exceptional phase stability of the OCT engine means that the Z-axis of the display (depth) has minimal jitter, in turn maximizing the real-time interpretability of the image. It also allows us to perform mathematical manipulation of the data that would otherwise be impossible. For example, one advantage of the systems described herein is the ability to perform pre-FFT averaging, which lowers the overall noise floor of the system again translating directly to image quality and interpretability.

In one example, the catheter is around 2 mm in diameter (7F compatible). In a saline-filled lumen, the system will be able to detect an interface (e.g., vessel wall) at 2 mm from the OD of the catheter. In this variation, the following parameters may be used for the catheter and system:

| Specifications | Value |
| --- | --- |
| Optimized Detector Bandwidth | DC - 10 MHz |
| Nyquist/Shannon rate | 20 MHz |
| Minimum number of points to sample for full resolution | 630 |

The detector may detect optical modulation on the carrier wave from DC to at least 10 MHz with no roll-off in sensitivity. To prevent aliasing (which complicates image interpretation) we may digitize the detector output at a minimum of 20 M-Samples/sec (Nyquist limit) to preserve interpretable real time imaging capability. We may thus capture at least 630 points per laser pulse at this digitizer rate to avoid undersampling the available laser bandwidth.

A practical resolution target is the intima of healthy coronary artery. The system resolution is capable of showing the intima (endothelial layer+internal elastic lamina) as a single sharp bright line on the display.

The system may have an impulse response of 8-10 microns. This resolution dictates the laser scan range requirements and the bandwidth requirements of all the optical components in the fiber harness through the equation:

$$\delta z = \frac{2\ln 2}{\pi} \frac{\lambda_0^2}{n\Delta\lambda}$$

Where $\delta z$ is the axial resolution, $\lambda$ is the wavelength, $\Delta\lambda$ is the wavelength range over which the laser scans, n is the refractive index of the medium and the other symbols have their usual meaning. The origin of this relationship is the Heisenberg Uncertainty Principle. Several observations accrue from this equation.

If the laser scan range $\Delta\lambda$ is not broad enough, $\delta z$ (the resolution) is compromised and an image of a step refractive index discontinuity will be blurred out over many pixels. If any of the optical components in the system restrict (alternatively called clipping or vignetting) the effective bandwidth of the system is reduced and the resolution may suffer. Since the resolution equation has the center wavelength squared in the numerator, as we move to longer center wavelengths for the reasons described above, commensurately larger laser scan range may achieve equivalent axial resolution. Opthalmology is routinely performed at 800 or 1000 nm center wavelength where there is no need to image deeply into the retina but where the available lasers allow extremely high resolution of the layers of the retina (down to 1-2 microns thickness).

In some variations, the OCT system has a scan range of >100 nm. The theoretical resolution of this engine is 6.35 microns in a medium with a refractive index of 1.35. Stipulating that we digitize at least at the Nyquist limit, fully sample the scanned bandwidth, and that the resealing procedure in the software does not distort the data, the theoretical resolution of this system is sufficient to show the intima of a healthy coronary at the impulse response limit.

The choice of 1310 nm as a center wavelength for the laser means that we may use standard commercial off-the-shelf telecommunications components which have guaranteed performance at this wavelength and for which standardized test protocols exist. Reasonable and customary incoming inspection procedures can be used to verify that the components going into the system will not deteriorate image quality.

As mentioned above, the system may include receiving electronics including a detector. Assuming that the operating center wavelength is 1315-1340 nm with a full-width half maximum responsivity of >100 nm, and that the detector operates as close as reasonably possible to the shot-noise limited regime, the system may have sufficient trans-impedance gain from the detector to allow the A/D card to operate at an input range where digitizer noise is not a dominant contributor to the noise floor of the system.

Manufacturing tolerances on the catheters will yield a range of distal tip reference reflection intensities. The detector may be configured or chosen so as not to saturate at the high manufacturing limit of the reference reflection power. In one example, the system uses a Fermionics FD80 photodiode in an FC receptacle package as the active element in the photodetector.

The system may also include a fiber harness designed to: 1) provide a low loss pathway from the laser to the catheter, 2) route signal light returning from the catheter to the detector, 3) allow the bleed-in of a red laser diode signal to allow rapid assessment of the integrity of the fiber from cable to distal tip, and 4) provide manufacturing, calibration and field service housekeeping signals to facilitate console production, validation and maintenance.

Figure 9:
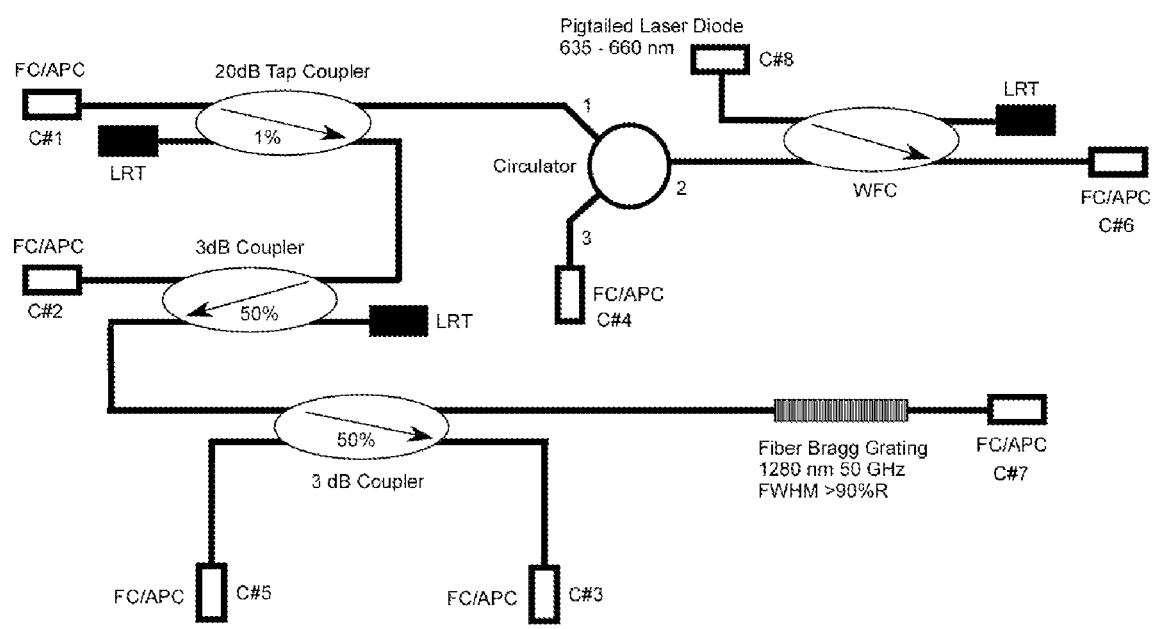
FIG. 9 shows one example of an optical circuit.

One primary component of the fiber harness may be a self-contained enclosure with bulkhead FC/APC receptacles on it and containing an optical circuit (such as the one shown in FIG. 9. In one example, the fiber harness may be connected as: #1 Incoming OCT source (e.g., Santec) Santec output connected here. #2 Diagnostic port (OSA/Photodiode/MZI Calibration); #3Diagnostic port (OSA/Photodiode/MZI Calibration); #4 Connection to Detector; #5 Reflected FBG Marker (Time/Wavelength Calibration Point); #6 Connection to Catheter; #7 Transmitted FBG Signal (Photodiode scope trigger); #8Connection to red laser source. Connections may be made with single mode fiber with a cut-off of <1260 nm. The inputs/outputs do not need to be optically isolated.

In some variations, an electrical harness may be used. The electrical harness may be configured to: 1) provide isolation for the various electrical components in the imaging system; 2) distribute 110V to the OCT engine, slave monitor and computer; 3) provide regulated isolated housekeeping power at appropriate voltages and amperages to the detector, red diode laser, catheter handle azimuthal position encoder; 4) send the video signal to the remote monitor; and 5) receive the catheter handle azimuthal angle encoder signal back to the console.

Line power may enter the console through a standard IEC60320 type C14 male power cord entry connector. The power cord used may be Hospital Grade and may have a standard IEC60320 type C13 female connector at the console end. An isolation transformer can distribute LINE power to the OCT engine, slave monitor and computer through IEC standard power cords.

Figure 10:
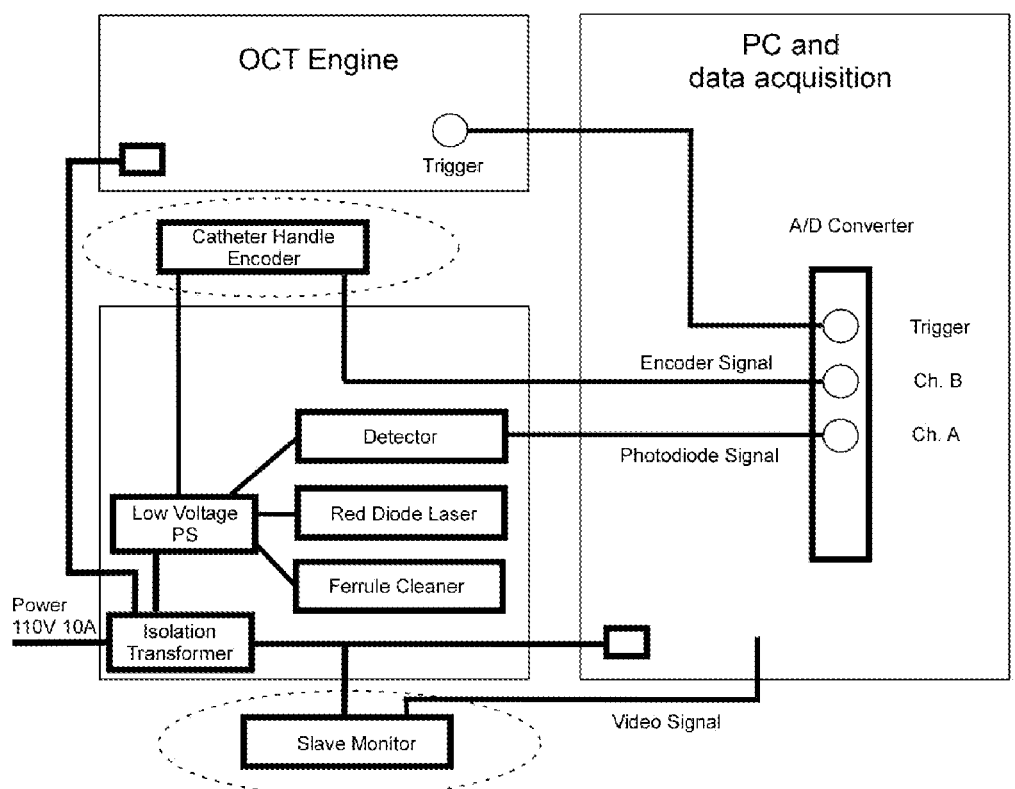
FIG. 10 is a schematic of an OCT system as described herein.

FIG. 10 shows one example of a schematic of an OCT system as described herein. In this example, Items with dotted perimeters are outside the main console chassis enclosure. Analog signal interconnects are to be made with RG58 (U, A/U) patch cables terminated with BNC connectors. The (Santec) Trigger Out signal is a falling edge signal (high Z) and should not be terminated in 50 ohms. The Encoder Signal should be terminated with a MiniCircuits low pass filter module at the A/D card to remove high frequency spurious noise. The Detector Signal should be terminated with a MiniCircuits low pass filter module at the A/D card to remove any noise in an irrelevant frequency range.

Figure 11:
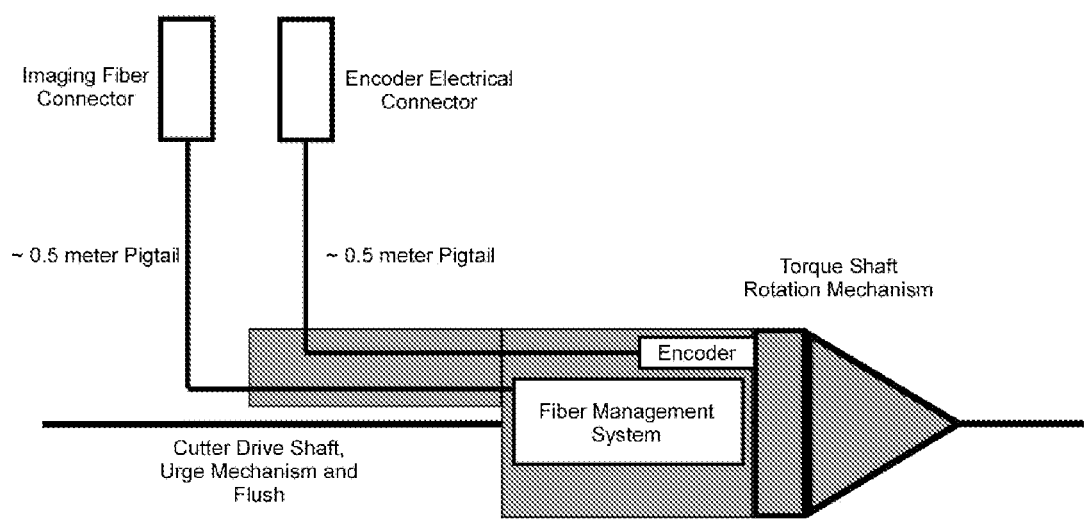
FIG. 11 illustrates one variation of a handle, including fiber management (spool) elements.
Figure 12:
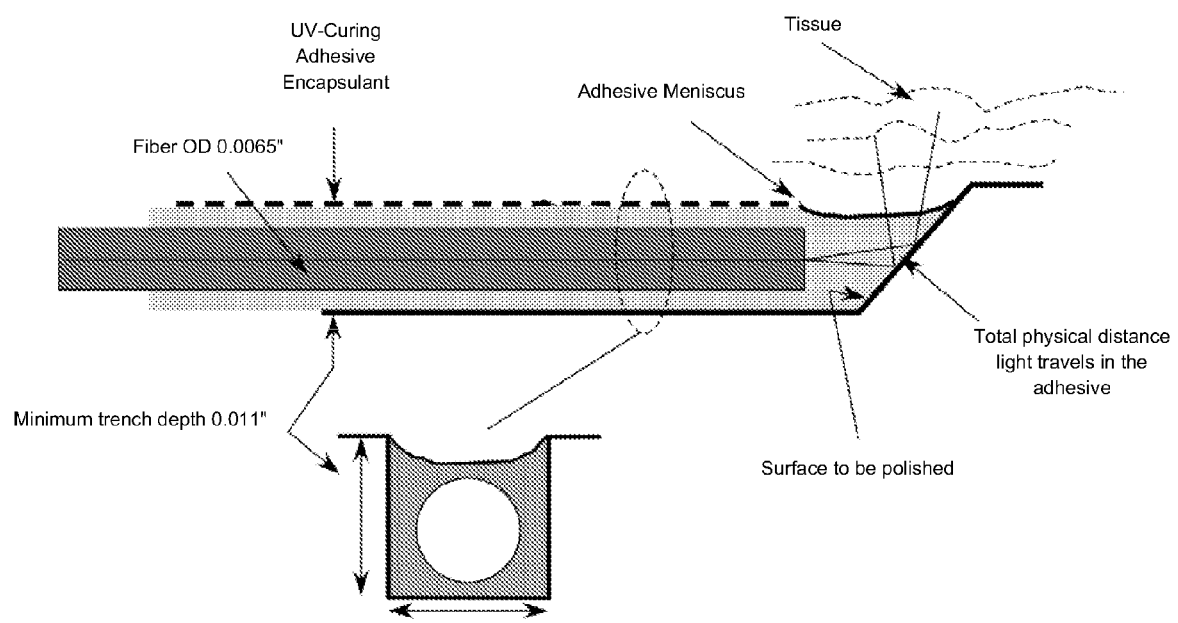
FIG. 12 illustrates one example of the distal end of a catheter as described herein.

FIG. 11 illustrates one variation of a handle, shown schematically. FIG. 12 illustrates one example of the distal end of a catheter as described herein. In this example, the distal end of the catheter includes a fiber having a core that is embedded in a transparent medium as described above. The fiber has an OD of 0.0065" and is polyimide coated and flat-cleaved (at90°). The polyimide is stripped from the end to about 500 microns. The mis-match between the refractive indexes of the core and the embedding medium gives a 32-35 dB return loss after curing.

The optical fiber may have a cut-off less than 1260 nm and have single mode performance between 1270 and 1380 nm (and be manufactured compatible with SMF-28 standards). Dissimilar fibers are not preferred as they may populate higher-order spatial modes or generate spurious return loss>65 dB at any given event. The mechanical connections (pigtail and patch cable) may include a simplex cable, and an inner loose tube Teflon Aramid fiber inner annulus to prevent stretching. The outer Jacket may be 2 mm polyurethane. The connector may be a Diamond E2108.6 connector with a 0.25 dB maximum insertion loss and a −65 dB maximum return loss.

The distal tip reference reflection (mirror) may include at least one (1) reflective interface, and may have a return loss of −33.5 dB (Nominal (31-35 dB)). There may be 200-250 microns solid transparent offset from interface to minimum tissue approach point. Interceding optical discontinuities between console and catheter distal tip may be kept to less than 65 dB return loss maximum for any individual surface. The number of reflective interfaces separated by less than 8 mm may be minimized. The parameters above are exemplary only, and may be varied as understood by those of skill in the art, while still remaining in the spirit of the invention as described herein.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for optical coherence tomography, comprising:
   a source of optical radiation;
   an optical fiber having a core providing a common path for optical radiation reflected from a reference interface and a target, the core having a first refractive index;
   receiving electronics configured to receive the optical radiation reflected from the reference interface and the target;

an interface medium at the reference interface and in physical and optical contact with the optical fiber, the interface medium having a second refractive index, wherein the first refractive index and the second refractive index are mismatched so as to adjust the optical radiation reflected from the reference interface such that the receiving electronics operate in a total noise range that is within 5 dB of a shot noise limit; and a processor configured to generate an image of the target based upon the optical radiation received by the receiving electronics that are operating within 5 dB of the shot noise limit.

2. The system of claim 1, wherein the first refractive index and the second refractive index are mismatched such that the receiving electronics operate in a total noise range that is within 3 dB of the shot noise limit.

3. The system of claim 1, wherein the first refractive index and the second refractive index are mismatched such that the receiving electronics operate in a total noise range that is within 2 dB of the shot noise limit.

4. The system of claim 1, wherein the source of optical radiation is a swept-frequency source.

5. The system of claim 1, further comprising a mirror in the interface medium, the mirror configured to reflect the optical radiation from the optical fiber to the target.

6. The system of claim 5, wherein the mirror comprises a gold-coated silicon die.

7. The system of claim 1, wherein the interface medium is a solid transparent medium.

8. The system of claim 1, wherein the interface medium is in physical and optical contact with a distal end of the core.

9. The system of claim 1, further comprising a directional element configured to relay the optical radiation from the source to a distal end of the core.

10. The system of claim 1, wherein the first refractive index $n_1$ and the second refractive index $n_2$ are mismatched such that:

$$\frac{P_{out}}{P_{in}} = \left(\frac{n_1 - n_2}{n_1 + n_2}\right)$$

wherein $P_{in}$ is the power of the optical radiation at the distal end of the optical fiber prior to entering the interface medium, and wherein $P_{out}$ is the power of the optical radiation reflected from the reference interface such that the receiving electronics operate in a total noise range that is within 5 dB of the shot noise limit.

11. The system of claim 10, wherein the first refractive index $n_1$ and the second refractive index $n_2$ are mismatched such that:

$$P_{det} = P_{out}(1-L)$$

wherein L is the sum of all the optical losses from the distal end of the probe to the receiving electronics and $P_{det}$ is the power at the receiving electronics.

12. A catheter for use with optical coherence tomography, comprising:

an elongate catheter body;

an optical fiber in the elongate catheter body configured to connect to a source of optical radiation and receiving electronics, the optical fiber having a core providing a common path for optical radiation reflected from a reference interface and a target and to transmit the optical radiation to receiving electronics, the core having a first refractive index; and an interface medium at the reference interface and in physical and optical contact with the optical fiber, the interface medium having a second refractive index, wherein the first refractive index and the second refractive index are mismatched so as to adjust the optical radiation reflected from the reference interface such that the receiving electronics configured to receive optical radiation reflected from the reference interface and the target operate in a total noise range that is within 5 dB of a shot noise limit;

wherein the catheter is further configured to connect with a processor configured to generate an image of the target based upon the optical radiation received by the receiving electronics that are operating within 5 dB of the shot noise limit.

13. The catheter of claim 12, wherein the first refractive index and the second refractive index are mismatched such that the receiving electronics operate in a total noise range that is within 3 dB of the shot noise limit.

14. The catheter of claim 12, wherein the first refractive index and the second refractive index are mismatched such that the receiving electronics operate in a total noise range that is within 2 dB of the shot noise limit.

15. The catheter of claim 12, further comprising a mirror in the interface medium, the mirror configured to reflect the optical radiation from the optical fiber to the target.

16. The catheter of claim 15, wherein the mirror comprises a gold-coated silicon die.

17. The catheter of claim 12, wherein the interface medium is a solid transparent medium.

18. The catheter of claim 12, wherein the interface medium is in physical and optical contact with a distal end of the core.

19. The catheter of claim 12, wherein the first refractive index $n_1$ and the second refractive index $n_2$ are mismatched such that:

$$\frac{P_{out}}{P_{in}} = \left(\frac{n_1 - n_2}{n_1 + n_2}\right)$$

wherein $P_{in}$ is the power of the optical radiation at the distal end of the optical fiber prior to entering the interface medium, and wherein $P_{out}$ is the power of the optical radiation reflected from the reference interface such that the receiving electronics operate in a total noise range that is within 5 dB of the shot noise limit.

20. The catheter of claim 19, wherein the first refractive index $n_1$ and the second refractive index $n_2$ are mismatched such that:

$$P_{det} = P_{out}(1-L)$$

wherein L is the sum of all the optical losses from the distal end of the probe to the receiving electronics and $P_{det}$ is the power at the receiving electronics.

21. A method of performing optical coherence tomography, comprising:

transmitting optical radiation from a source through an optical fiber having a core, the core having a first refractive index;

transmitting the optical radiation from the optical fiber through an interface medium, wherein the interface medium is in physical and optical contact with the optical fiber, the interface medium having a second refractive index;

transmitting optical radiation reflected from the target and reflected from a reference interface along a common path in the optical fiber to a detector;

receiving the reflected optical radiation at receiving electronics, wherein the first refractive index and the second refractive index are mismatched so as to adjust the optical radiation reflected from the reference interface such that the receiving electronics operate in a total noise range that is within 5 dB of a shot noise limit; and generating an image of the target based upon the reflected optical radiation received by the receiving electronics that are operating within 5 dB of the shot noise limit.

22. The method of claim 21, wherein the first refractive index and the second refractive index are mismatched such that the receiving electronics operate in a total noise range that is within 3 dB of the shot noise limit.

23. The method of claim 21, wherein the first refractive index and the second refractive index are mismatched such that the receiving electronics operate in a total noise range that is within 2 dB of the shot noise limit.

24. The method of claim 21, wherein transmitting optical radiation comprises transmitting swept-source radiation.

25. The method of claim 21, wherein transmitting the optical radiation from the optical fiber through the interface medium further comprises transmitting the optical radiation from the optical fiber to a mirror in the interface medium.

* * * * *